(12) United States Patent
Wagner

(10) Patent No.: US 7,124,032 B2
(45) Date of Patent: Oct. 17, 2006

(54) SYSTEM AND METHOD FOR RECONSTRUCTING PATHWAYS IN LARGE GENETIC NETWORKS FROM GENETIC PERTURBATIONS

(75) Inventor: Andreas Wagner, Albuquerque, NM (US)

(73) Assignee: Science & Technology Corporation @ UNM, Albuquerque, NM (US)

( * ) Notice: Subject to any disclaimer, the term of this patent is extended or adjusted under 35 U.S.C. 154(b) by 612 days.

(21) Appl. No.: 10/140,323

(22) Filed: May 7, 2002

(65) Prior Publication Data

US 2003/0023388 A1 Jan. 30, 2003

Related U.S. Application Data

(60) Provisional application No. 60/289,301, filed on May 7, 2001.

(51) Int. Cl.
*G01N 33/48* (2006.01)
*G06F 19/00* (2006.01)

(52) U.S. Cl. .......................................... 702/19; 702/27
(58) Field of Classification Search .................. 702/19, 702/27
See application file for complete search history.

(56) References Cited

OTHER PUBLICATIONS

Kuffner et al., Bioinformatics, vol. 16, No. 9, pp. 825-836,2000.*
Joseph L. DeRisi et al., 1997 Exploring the Metabolic and Genetic Control of Gene Expression on a Genomic Scale. Science, vol. 278: 680-686.
Michael B. Eisen et al, 1998 Cluster Analysis and Display of genome-wide expression patterns. Proceedings of the National Academy of Sciences of the United States of America, vol. 95:14863-1488.
Andreas Wagner. The Yeast Protein Interaction Network Evolves Rapidy and Contains Few Redundant Duplicate Genes. Molecular Biology and Evolution, vol. 18(7): 1283-1292, (2001).
Saeed Tavazoie et al, 1999 Systematic Determination of Genetic Network Architecture. Nature Genetics, vol. 22: 281-285.

* cited by examiner

*Primary Examiner*—Tim Vo
*Assistant Examiner*—Cheyne D. Ly
(74) *Attorney, Agent, or Firm*—Baniak Pine & Gannon

(57) ABSTRACT

A system and method for reconstructing pathways in large genetic networks from genetic perturbations comprises an analysis method and system that applies a recursive algorithm for determining the path between every gene pair in an arbitrarily large genetic network from large-scale gene perturbation data and reconstructs all direct and indirect regulatory gene interactions in the network. Graph theory mathematics is applied to genetic network reconstruction in the following manner: Genetic perturbation data is used to identify all genes accessible from a perturbed gene to generate an accessibility list for the gene. Graph theory mathematics is applied to the accessibility list and its graph to determine a condensation of the graph as defined by the condensation's accessibility list. Graph theory mathematics is applied to the accessibility list, such as through a recursive algorithm performed on a desktop computer, to obtain an adjacency list for the gene that characterizes a genetic network.

12 Claims, 13 Drawing Sheets

```
1    for all nodes u of G
2        if node u has not been visited 3            call MAXPATH(u)
4        end if 5    MAXPATH(u)
6        for all nodes v∈Acc(u)
7            if Acc(v)=∅
8                declare v as visited.
9            else
10               call MAXPATH(v)
11           end if
12           p(u,v)=1

13       for all nodes v∈ Acc(u)
14           for all nodes w∈ Acc(v)
15               p(u,w)=max(p(u,w), 1+p(v,w))
16   p(u,u)=0
17   declare node u as visited
18   end MAXPATH(u)
```

Fig. 3

```
1       for all nodes i of G
2           Adj(i)=Acc(i)

3       for all nodes i of G
4           if node i has not been visited
5               call PRUNE_ACC(i)
6           end if 7       PRUNE_ACC(i)
8           for all nodes j ∈ Acc(i)
9               if Acc(j)=∅
10                  declare j as visited.
11              else
12                  call PRUNE_ACC(j)
13              end if 14          for all nodes j ∈ Acc(i)
15              for all nodes k ∈ Acc(j)
16                  if k ∈ Acc(i)
17                      delete k from Adj(i)
18                  end if
19          declare node i as visited
20      end PRUNE_ACC(i)
```

```
1       for all nodes i of G
2           if component[i] has not been defined
3               create new node x of G*
4               component[i]=x
5               for all nodes j ∈Acc(i)
6                   if i ∈Acc(j)
7                       component[j]=x
8                   end if
9           end if 10      for all nodes i of G*
11          Acc_G*(i)=∅
12      for all nodes i of G
13          for all nodes j ∈ Acc(i)
14              if component[i] ≠ component[j]
15                  if component[j] ∉Acc_G*(component[i])
16                      add component[j] to Acc_G*(component[i])
17                  end if
18              end if
```

SYSTEM AND METHOD FOR RECONSTRUCTING PATHWAYS IN LARGE GENETIC NETWORKS FROM GENETIC PERTURBATIONS

RELATIONSHIP TO PRIOR APPLICATIONS

This application claims the benefit of U.S. Provisional Application No. 60/289,301, filed May 7, 2001, which is incorporated herein by reference in its entirety.

FIELD OF THE INVENTION

The present invention is a system and method for reconstructing pathways in genetic networks from genetic perturbations. More particularly, the present invention comprises an analysis method that applies a recursive algorithm for determining the paths between gene pairs in a genetic network from gene perturbation data and reconstructs all measurable direct and indirect regulatory gene interactions in the network by applying graph theory mathematics to genetic networks.

BACKGROUND OF THE INVENTION

Most techniques to analyze genetic networks monitor changes in the expression of many genes under changing environmental conditions, in different physiological stages, or in different genetic backgrounds to identify genes with similar expression in order to cluster them. However, this approach suffers from the problem that correlated expression can only point to regulatory interactions between genes. It cannot be used to infer such interactions. In addition the number of modules and the number of isolated genes inferred from correlated expression are likely underestimates, because gene perturbation studies preferentially perturb a sample of interesting regulatory genes with many interactions and not an unbiased random sample.

SUMMARY OF INVENTION

It is an objective of the present invention is to identify pathways connecting genes in the network.

It is another object of the present invention to apply graph theory mathematics to the field of genetic networks to produce adjacency lists that describe the genetic interactions of gene networks based on gene perturbation data.

Another objective of the present invention is to identify which genes in a network directly or indirectly influence the activity of other genes in the network.

Yet another objective of the present invention is to reconstruct all measurable direct and indirect interactions in a network.

A further objective of the present invention is to reconstruct genetic pathways from gene perturbation data.

Another objective of the present invention is to automate the process of reconstructing gene pathways in networks of arbitrary size and complexity.

Yet another objective of the present invention is to reconstruct networks of gene interactions that change during different developmental stages.

A further objective of the present invention is to reconstruct networks of gene interactions that change during different physiological states.

Another objective of the present invention is to reconstruct networks of gene interactions that change in different environmental conditions.

Another objective of the present invention is to reconstruct networks of gene interactions that change between cell types.

Another objective of the present invention is to identify master regulators in the gene pathway.

Another objective of the present invention is to identify target genes, groups of genes, and genetic regulatory interactions that are of interest in genomics, proteomics, protein function, drug development, disease progression, agriculture and other activities as they relate to genomic proteons, etc.

Another objective of the present invention is to identify the most parsimonious gene pathway in normal and disease states for development of drug discovery.

Another objective of the present invention is to identify gene pathways for host defense in plants.

Another objective of the present invention is to identify gene pathways in plants responsible for insecticidal activity.

Another objective of the present invention is to identify gene pathways in plants that are responsible for reproduction.

Another objective of the present invention is to identify gene pathways in plants that are responsible for drought tolerance and virulence.

Another objective of the present invention is to identify genes that have pleiotropic effects when mutated.

A gene can affect the activity of other genes either directly or indirectly. For example, when overexpressing a transcription factor X, one might find that the expression levels of genes A and B change. Upon further investigation, one may find that X binds the upstream regulatory region of A and up-regulates its expression. This will be referred to as a direct effect of X on A. However, in the case of B, one might find that X induces the expression of a protein phosphatase, which dephosphorylates and thus inactivates a transcriptional repressor of B. This will be referred to as an indirect effect of X on B. To reconstruct a genetic network is to identify all direct effects of network genes on one another, within the limits of experimental resolution.

The present invention applies a system and method that can determine the direct and indirect pathways connecting genes in the network and which genes in a network influence the activity of which other genes directly for gene networks of an arbitrary number of genes. The algorithm's power to resolve regulatory gene interactions, and thus to resolve the causal structure of a genetic network requires different kinds of data than utilized by existing methods. Specifically, it requires perturbation of many genes in a network. The required large-scale data is now becoming available in a variety of model organisms.

A particular advantage of the present invention is that it can decrease research costs since it allows use of only a single perturbation per gene to map the genetic network (i.e., a knockout), although other methods using two or more perturbations (i.e., a double knock out, etc.) can be used to resolve network loops. Additionally, the present invention can be performed on a minimal personal computer in a very short period of time using standard microarray data. The present invention is useful in targeting genes, groups of genes, etc., that are of interest in proteomics or protein function, drug development, and disease progression, agricultural biotechnology and other relationships.

The present invention is especially useful for prioritizing such gene groups or subgroups (relative to less desirable groups) that are likely to have greater complexity and problems. Often these gene groups are associated with drug discovery. Identifying the pathways connecting genes in the network and which genes in a network influence the activity of which other genes directly are some of the most fundamental question about the structure of a large genetic network.

Definitions

As used herein, a genetic network is defined as a group of genes in which individual genes can change the activity of other genes.

Change of gene activity as used herein includes many different things, such as changes in DNA methylation, gene expression—on the mRNA or protein level—, alternative splicing, post-transcriptional regulation, or post-translational modification, such as phosphorylation.

As used herein, a genetic perturbation is an experimental manipulation of gene activity through either the gene itself or its product. Genetic perturbations can be achieved through recombination, point mutation, gene deletion, overexpression, underexpression, post translational modifications, inhibition of transcription and translation, for example by using antisense RNA, or any other interference with the translation of mRNA or the activity of the product, including any covalent modification or non-covalent modification. Although mutations are not usually thought of as manipulations of gene activity, the present invention views them as such. Other methods of gene perturbation are well known to those of skill in the art and the present invention does not limit itself to those disclosed herein.

A master regulator is a gene that drives large parts of a physiological or developmental gene network.

Accessiblity list is a compilation of all the genes whose activity can be accessed (influenced in their activity state) by a genetic perturbation of a gene located in the network.

Adjacency list is a list of all regulatory interactions between genes in a network and completely identifies all genes that the genetic perturbation affects directly.

Algorithm robustness is the ability of an algorithm to reconstruct an adjacency list despite errors in the input data.

Graphs are mathematical objects consisting of nodes and edges; in the context of gene networks, nodes correspond to genes and edges correspond to regulatory interactions among genes.

Paths are sequences of edges connecting adjacent nodes.

Cyclic graphs are graphs that contain paths that start at one node and lead back to the same node.

Acyclic graphs are graphs without cycles.

Directed graphs or digraphs are mathematical objects consisting of nodes and directed edges.

An Adjacency list of gene i a list of genes whose activity is directly influenced by gene i.

An Accessibility list of a gene is a list of direct and indirect causal interactions obtained by following all paths leaving the gene.

Although the invention as described utilizes mRNA expression as measured by micro-arrays, and its change in response to a genetic perturbation, the principal idea applies to any notion of gene activity.

BRIEF DESCRIPTION OF THE DRAWINGS

FIG. 1A illustrates a graph representation of a hypothetical genetic network G of 21 genes.

FIG. 1B illustrates an alternative representation of the network shown in FIG. 1A.

FIG. 1C illustrates list of direct and indirect causal interactions of the network shown in FIG. 1A.

FIG. 2C is acyclic and FIG. 2D is cyclic.

FIG. 3 illustrates a one embodiment of the recursive algorithm of the present invention.

FIG. 10A contains two nontrivial strong components, that comprising nodes 1, 3, 4, 5, 15 (diamonds), and that comprising nodes 6, 9 and 12 (squares). In the condensation of this graph, shown in FIG. 10B), the strong components are collapsed onto a single node.

DETAILED DESCRIPTION OF THE INVENTION

Figure 1:
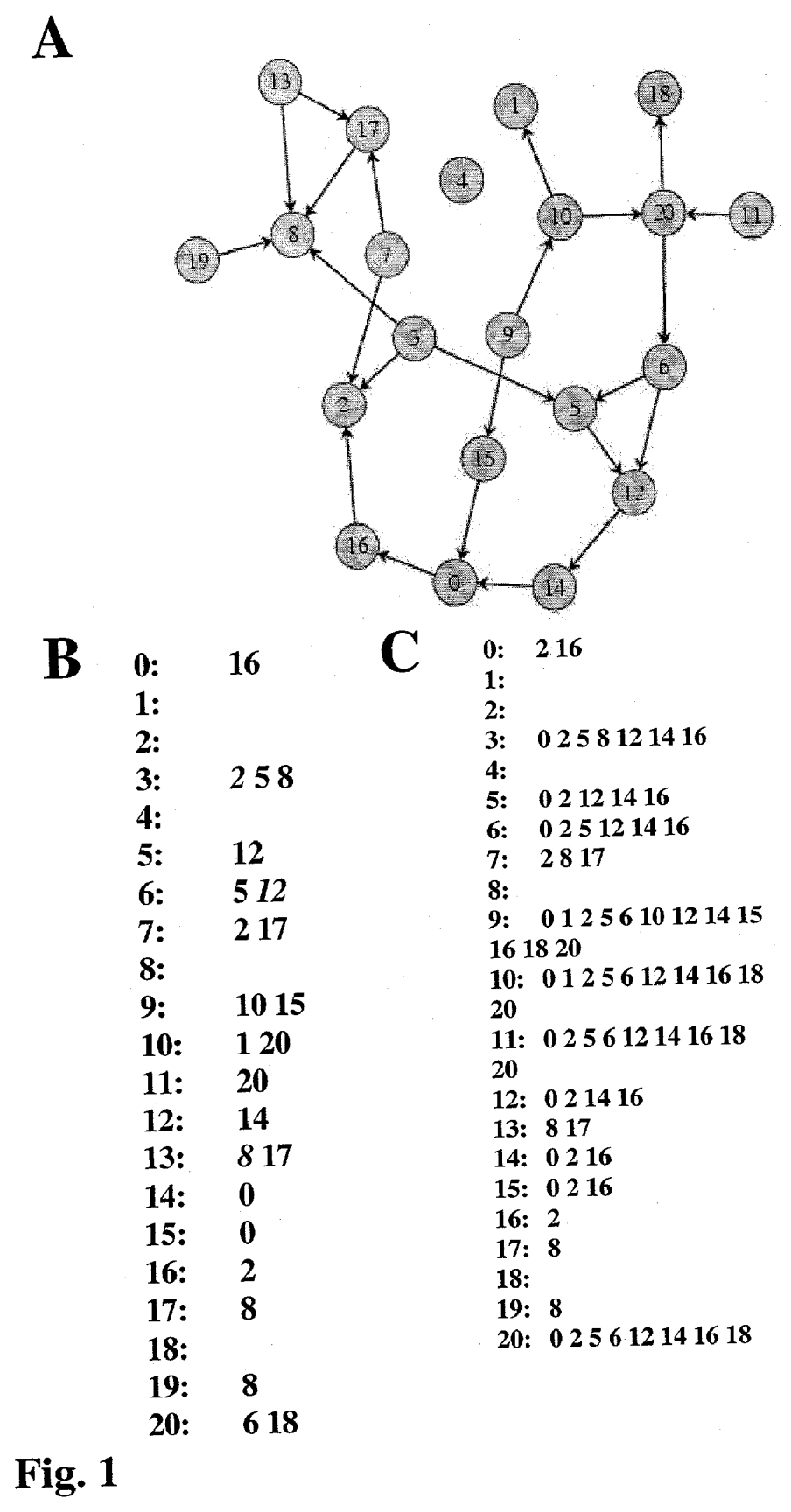
Figure 2:
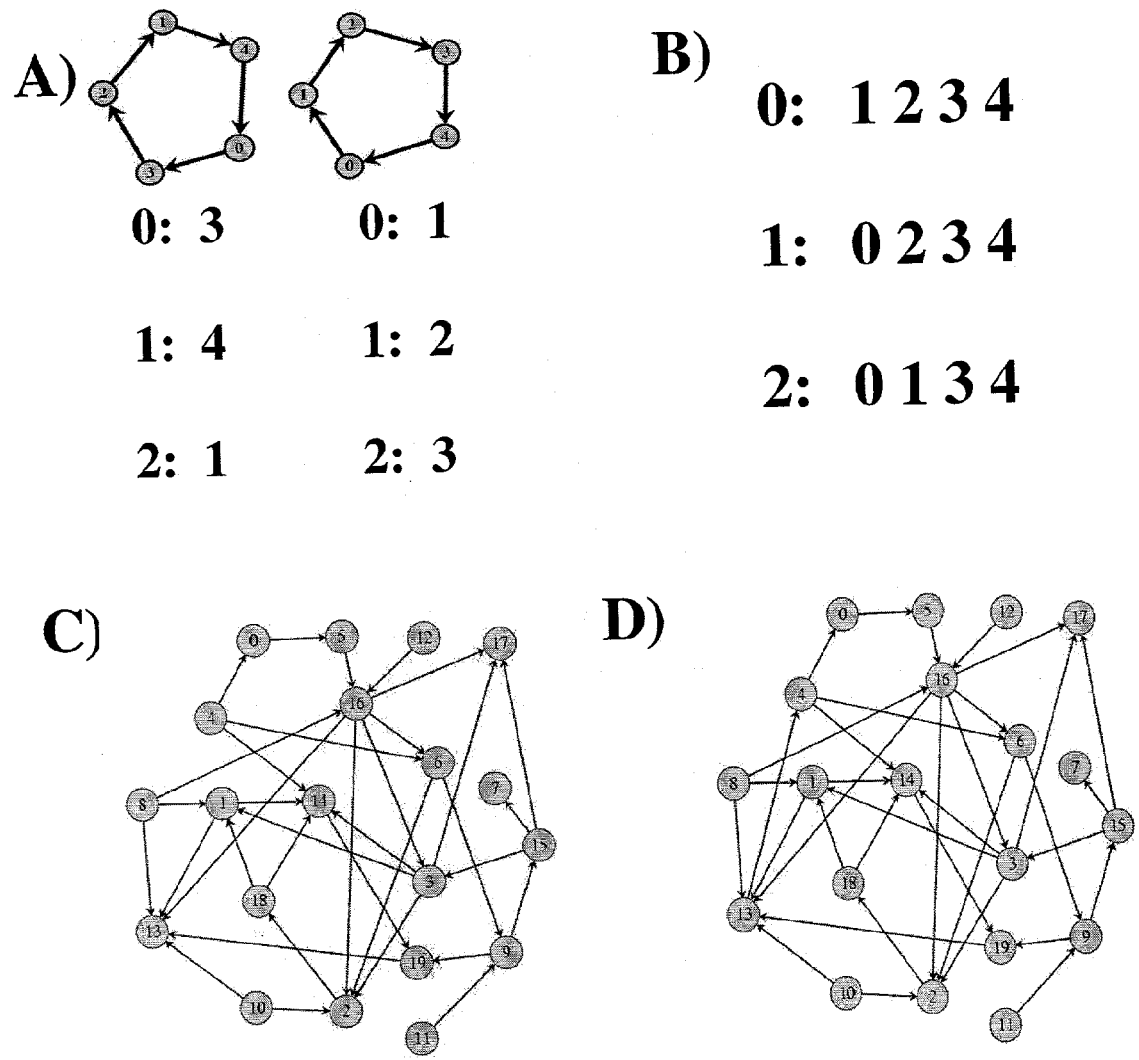
FIG. 2A illustrates two simple cyclic networks.
FIG. 2B illustrates the accessibility list generated when the networks of FIG. 2A are perturbed.
FIGS. 2C and FIG. 2D illustrate two similar 20 gene networks where

Because the available technology to measure gene expression is associated with great amounts of experimental noise, the description of present invention will be limited to qualitative information on how genetic perturbations affect gene expression. That is, when manipulating the activity of one gene, what other genes are affected in their expression? Qualitative information on gene interactions lends itself ideally to a graph representation of genetic networks. A directed graph or digraph is a mathematical object consisting of nodes and directed edges. In a graph representation of a genetic network, the nodes of the graph correspond to genes, and two genes, say gene 1 and gene 2, are connected by a directed edge (an arrow, 1→2) if gene 1 influences the activity of gene 2 directly. FIG. 1A illustrates a graph representation of a hypothetical genetic network G of 21 genes whose nodes correspond to genes numbered from 0 through 20. FIG. 1B shows an alternative representation of the network shown in 1A. For each gene i, FIG. 1B contains a list of genes whose activity is directly influenced by gene i. This list is called the adjacency list Adj(i) of i. Adj is the adjacency list of G. One might also call it the list of direct regulatory interactions. It completely defines the structure of the network.

Genetic perturbation experiments cannot distinguish direct from indirect interactions. That is, when perturbing a gene in the network shown in FIG. 1A, one identifies all genes that this perturbation affects directly or indirectly, as its effects ripple through the network. For example, gene 0 influences, directly or indirectly, the activity of genes 2 and 16. Gene 1 does not influence the activity of any other gene, but its activity is influenced by genes 9 and 10. Gene 4 is an isolated node in this network. Its activity is neither influenced by any gene in the network, nor does it influence the activity of any gene. Starting from a graph representation of the network in FIG. 1A, one arrives at the list of direct and indirect causal interactions in FIG. 1C by following all paths leaving a gene. This list is also called the accessibility list Acc of a graph. because it shows all nodes (genes) that can be accessed (influenced in their activity state) from a given node by following paths of direct interactions. In the context of a genetic network one might also call it the list of perturbation effects or the list of regulatory effects. For each perturbed gene i, Acc(i) denotes the list of affected genes.

Generating the list in FIG. 1C from 1A or 1B is straightforward. The present invention addresses the more difficult problem of reconstructing all direct interactions in a network from all indirect ones, that is, to reconstruct 1A (Adj) from 1C (Acc), and to do that automatically for very large networks comprising thousands of genes. Genome scale perturbation experiments are beginning to provide the raw material for this endeavor. Its significance is best viewed in relation to the main thrust of molecular genetics, which uses genetic perturbations to reconstruct biochemical pathways involving painstaking gene-by-gene analysis. Automating such reconstruction for networks of thousands of genes would not only facilitate this task, but take it to a completely different scale.

This disclosure briefly reviews some standard terminology as well as some relevant theorems. For present purposes, graphs are best divided into two classes, those with and without cycles. A cycle is a path starting at a node and leading back to the same node. Graphs without cycles are called acyclic graphs. The problem that networks with cycles pose for reconstruction is illustrated in FIG. 2A with two simple cyclic networks. The order of direct regulatory interactions in these two networks is different, as reflected in the adjacency lists shown. However, both networks, when perturbed, would generate the accessibility list shown in FIG. 2B. Characteristically, perturbation of any gene influences the activity of all other genes in such a cyclic network (FIG. 2B). Thus, all possible orders of the five genes in a cycle are consistent with the accessibility list of FIG. 2B. Notice that this is not an algorithmic but an experimental limitation. Single gene perturbations cannot resolve gene orders in a cycle.

One might think that acyclic graphs must be rather simple objects. This is not so. Consider the two networks of 20 genes shown in FIG. 2C and FIG. 2D. They differ by only one edge: The network in FIG. 2D has a directed edge from gene 13 to gene 4 that is missing in FIG. 2C. The network in FIG. 2D is cyclic (e.g., it contains the cycle 4→6→9→19→13→4). The network in FIG. 2C is acyclic. Thus, the distinction between cyclic and acyclic networks need not be obvious.

Statistical inference from the perturbation response of transcriptional regulatory networks suggests that such networks are sparse, containing on average less than one direct regulatory interaction per gene. And biological networks whose coarse scale structure has been analyzed resemble sparse random networks with a scale-free degree distribution. Together, these observations suggest, albeit not conclusively, that gene networks may not be rife with cycles.

Cycles in networks must be addressed. The first step is to identify all cycles, and then collapse all nodes that are part of a cycle. The remaining network is acyclic and can be reconstructed as described below. More precisely, a strongly connected component or strong component of a directed graph G is a maximal subset of nodes of G in which every two nodes are mutually accessible. (This implies that there is a cycle through any two nodes of a strong component.) The present inventor has recently described an algorithm that identifies all strong components of a graph from its accessibility list, and generates from these components the condensation of the graph. The condensation G* of a directed graph G has the strong components of the graph G as its nodes. Denote the components of G (nodes of G*) as $S_1, \ldots, S_k$. There is an edge from any $S_i$ to any $S_j$ in G* if there is an edge in G from at least one node in the component $S_i$ to at least one node in the component $S_j$. To reconstruct a genetic network from single-gene perturbation experiments, one thus needs to identify all the strong components from the accessibility list generated by a perturbation experiment. The acyclic condensation thus obtained can be reconstructed as outlined below. If the network has no cycles to begin with, this step can be omitted and the original, acyclic network can be reconstructed directly.

An acyclic directed graph uniquely defines its accessibility list, but the converse is not true. In general, if Acc is the accessibility list of a graph, there may be many graphs G with Acc as their accessibility list. Among all these graphs, however, one has a unique property: it has the fewest edges. I call it the most parsimonious graph consistent with Acc. More precisely, the following theorem holds.

Theorem 1: Let Acc be the accessibility list of an acyclic digraph. Then there exists exactly one graph $G_{pars}$ that has Acc as its accessibility list (see Aho, A., *The transitive Reduction of a Directed Graph*, SIAM Journal on Computing, 1972, Vol. 1, pp. 131–137) and that has fewer edges than any other graph G with Acc as its accessibility list.

This graph has the property that it is shortcut-free.

Definition: Consider two nodes i and j of a digraph that are connected by an edge e. The range r of the edge e is the length of the shortest path between i and j in the absence of e. If there is no other path connecting i and j, then r:=∞. An edge e with range r≧2 but r≠∞ is called a shortcut.

Although the present invention is useful for genetic networks of all sizes, in a preferred embodiment, the present invention can be employed to reconstruct a large genetic network from n gene perturbations in fewer than $n^2$ steps. In this embodiment, an algorithm is disclosed to reconstruct direct regulatory interactions in gene networks from the effects of genetic perturbations on gene activity. Genomic technology has made feasible large-scale experiments that perturb the activity of many genes and then assess the effect of each individual perturbation on all other genes in an organism. Current experimental techniques cannot distinguish between direct and indirect effects of a genetic perturbation. An example of an indirect effect is a gene X encoding a protein kinase, which phosphorylates and activates a transcription factor Y, which then activates transcription of gene Z. X influences the activity of gene Y directly, whereas it influences Z indirectly. To reconstruct a genetic network means to identify, for each gene and within the limits of experimental resolution, the direct effects of a perturbed gene on other genes. One can think of this as identifying the causal structure of the network. The present algorithm performs this task for networks of arbitrary size and complexity. It is also based on a graph representation of a genetic network, as disclosed above. Algorithmic complexity in both storage and time is low, less than $O(n^2)$ such that, in practice, the algorithm can reconstruct networks of several thousand genes in mere CPU seconds on a desktop workstation.

Gene activity in the present example includes differences in post-transcriptional regulation, such as differential splicing, or post-translational modification, such as phosphorylation. It is well known that the activity of many gene products is regulated by phosphorylation, and gene products that phosphorylate or dephosphorylate other gene products are key regulators inside any living cell. Another aspect of gene activity is the methylation state of genes, which is related to gene silencing. And there are gene products that are involved in changing the methylation state of other genes. These few examples show that there are endlessly many possible ways of defining gene activity.

To reconstruct a genetic network is to identify all direct effects of network genes on one another's activity within the limits of experimental resolution.

Figure 6:
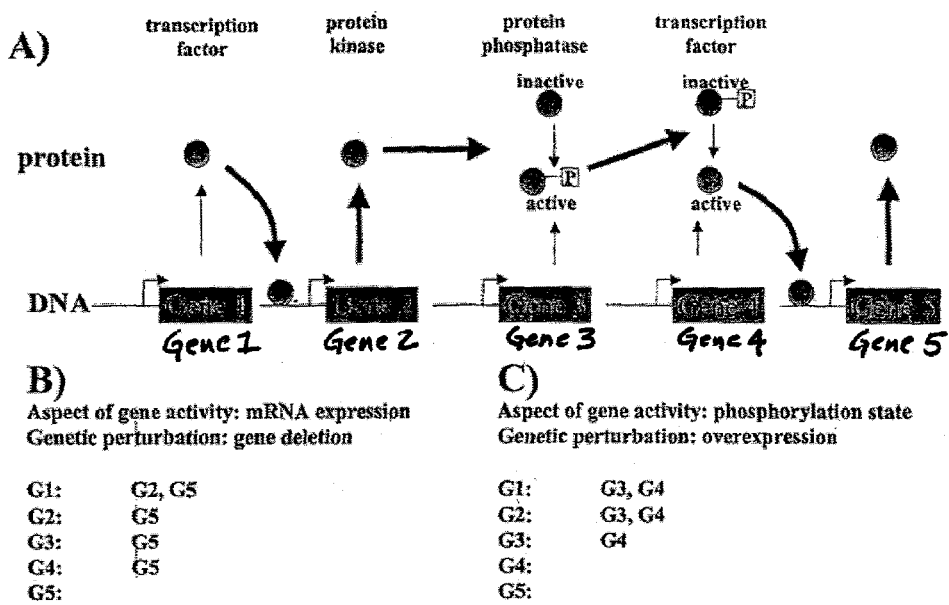
FIG. 6A illustrates a hypothetical biochemical pathway involving two transcription factors, a protein kinase, and a protein phosphatase, as well as the genes encoding them, B is a list of perturbation effects for each of the five genes in A, and C is analogous to B but for a different notion of gene activity (phosphorylation state).

The important issue of experimental resolution is best illustrated by the hypothetical example of a biochemical pathway shown in FIG. 6A. A constitutively expressed transcription factor produced by gene 1 induces expression of gene 2, whose product is a protein kinase. This protein kinase phosphorylates a protein phosphatase, the product of gene 3, an event that activates the phosphatase. The phosphatase in turn dephosphorylates a transcription factor, the product of gene 4. Dephosphorylation activates the transcription factor, which binds to and induces expression of gene 5, whose function is unspecified.

Now consider a hypothetical series of five different experiments, deleting each of the five genes involved in this pathway. For each of these five perturbations, we measure changes in gene activity. The notion of gene activity used here is that of the mRNA expression level. The results of these five hypothetical experiments are shown in FIG. 6B in a consistent format. Each line contains the results of one genetic perturbation. The leftmost symbol stands for the gene whose activity was manipulated, followed by a colon. To the right hand side of the colon, the names of genes appear whose activity was influenced by that particular manipulation. In the experiment whose result is shown in the first line of FIG. 6B, the activities (mRNA level) of genes 2 and 5 were affected by deleting gene 1. Gene 2 was affected because the product of gene 1 is required for transcription of gene 2. Gene 5 was affected, because, indirectly, the expression of gene 2 influences the phosphorylation state and the activity of the transcription factor produced by gene 4. When the product of gene 2 is absent, then the product of gene 4 will be inactive, and gene 5 will not be expressed. As opposed to its effect on the activities of genes 2 and 5, deletion of gene 1 does not affect the activity of genes 3 and 4. Deletion of gene 1 will only affect the phosphorylation state of genes 3 and 4, but not their mRNA expression, because they are constitutively expressed. The system and method of the present invention would identify the order in which the genes influence each others expression state (i.e. G1→G2→G5).

FIG. 6C shows a situation where the genetic perturbation is the same, but where the phosphorylation state is used as a measure of gene activity. Manipulation of gene 1 now does not affect the measured activity of genes 2 and 5, but it does affect the activities of genes 3 and 4. The system and method of the present invention would identify the order in which the genes influence each other's phosphorylation states (i.e. G1→G3→G4).

The system and method of the present invention is designed to reconstruct a genetic network from perturbation data and to distinguish direct from indirect regulatory effects. In a series of experiments in which the activity of every single gene in an organism is manipulated, (for instance, non-essential genes can be deleted, and for essential genes one might construct conditional mutants.), the effect on mRNA expression of all other genes is measured separately for each mutant. The result is a list similar to that shown in FIG. 6B, but for thousands of genes. The present invention would be able to identify all genes regulated directly by any transcription factor encoded in this organism's genome.

As above, the adjacency matrix of a graph G, $A(G)=(a_{ij})$. $A(G)$ is an n×n square matrix, where n is the number of nodes (genes) in the graph. An element $a_{ij}$ of this matrix is equal to one if and only if a directed edge exists from node i to node j. All other elements of the adjacency matrix are zero. Second, the accessibility matrix $P(G)=p_{ij}$ is also an n×n square matrix. An element $p_{ij}$ is equal to one if and only if a path following directed edges exists from node i to node j. $p_{ij}$ equals zero otherwise. Adjacency and accessibility matrices are the matrix equivalents of adjacency and accessibility lists.

Most real world graphs are sparse. That is, they have few outgoing edges per node. For such graphs, it is often more efficient to use lists rather than matrices for numerical operations. However, to state or prove theorems, matrix representations are sometimes more convenient.

In the following sections, an algorithm is developed in two steps to reconstruct a network from its accessibility list, as well as its mathematical foundation. First, restrict to graphs without cycles. In the second step, the present inventor will generalize to graphs with cycles. Before beginning, however, a problem germane to analyzing any kind of experimental data must be addressed. It is the problem that there are usually many possible and internally consistent reconstructions of a study system from experimental data. The preferred one is usually a simple or parsimonious one, by some suitable definition. Genetic network reconstruction is no exception to this rule.

Calculating the Most Parsimonious Network

Figure 7:
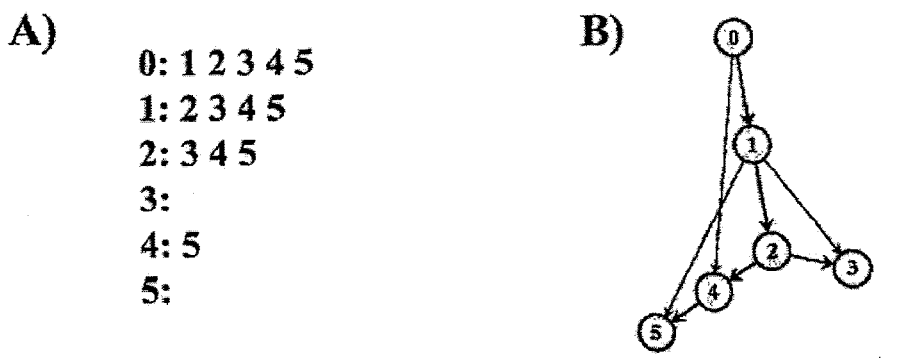
FIG. 7 illustrates the most parsimonious graph is the graph with the fewest edges consistent with a given accessibility list where A shows the accessibility Acc of an acyclic graph. B, C and D show graphs that have this accessibility list. The graph shown in D is the most parsimonious graph of Acc.
Figure 7:
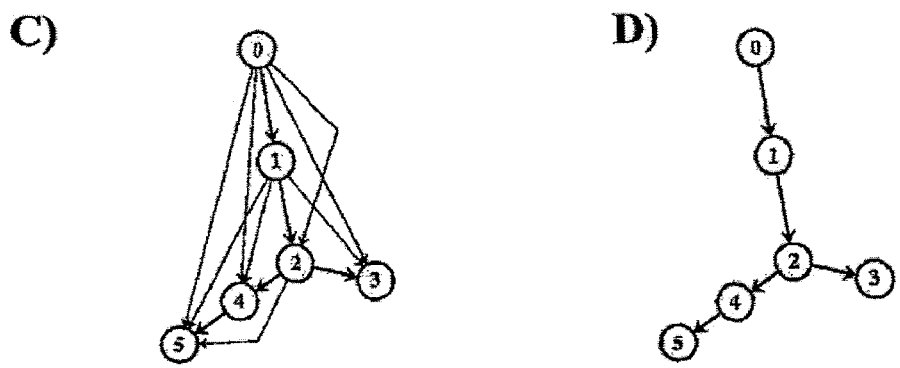

An acyclic directed graph defines its accessibility list, but the converse is not true. In general, if Acc is the accessibility list of a graph, there is more than one graph G with the same accessibility list. FIGS. 7A–D illustrate this with an example of three graphs (FIGS. 7B,C,D) with the same accessibility list Acc (FIG. 7A). For an example that simple it is obvious that there is one graph (FIG. 7D) that has Acc as its accessibility list and is simpler than all other graphs, in the sense that it has fewer edges. For more complicated graphs (FIG. 7C), it may not be so clear that there is always such a graph. In this section, the present inventor will thus prove that there exists exactly one such graph. In terms of reconstructing a genetic network, this means that for any list of perturbation effects there exists exactly one genetic network G with fewer edges than any other network with the same list of perturbation effects.

Theorem 1: Let Acc be the accessibility list of an acyclic digraph. Then there exists exactly one graph $G_{pars}$ that has Acc as its accessibility list and that has fewer edges than any other graph G with Acc as its accessibility list.

Calling $G_{pars}$ the most parsimonious network compatible with Acc.

Definition: An accessibility list Acc and a digraph G are compatible if G has Acc as its accessibility list. Acc is the accessibility list induced by G.

Definition: Consider two nodes i and j of a digraph that are connected by an edge e. The range r of the edge e is the length of the shortest path between i and j in the absence of e. If there is no other path connecting i and j, then $r:=\infty$.

Definition: An edge e with range $r \geq 2$ but $r \neq \infty$ is called a shortcut.

Figures 8, 9:
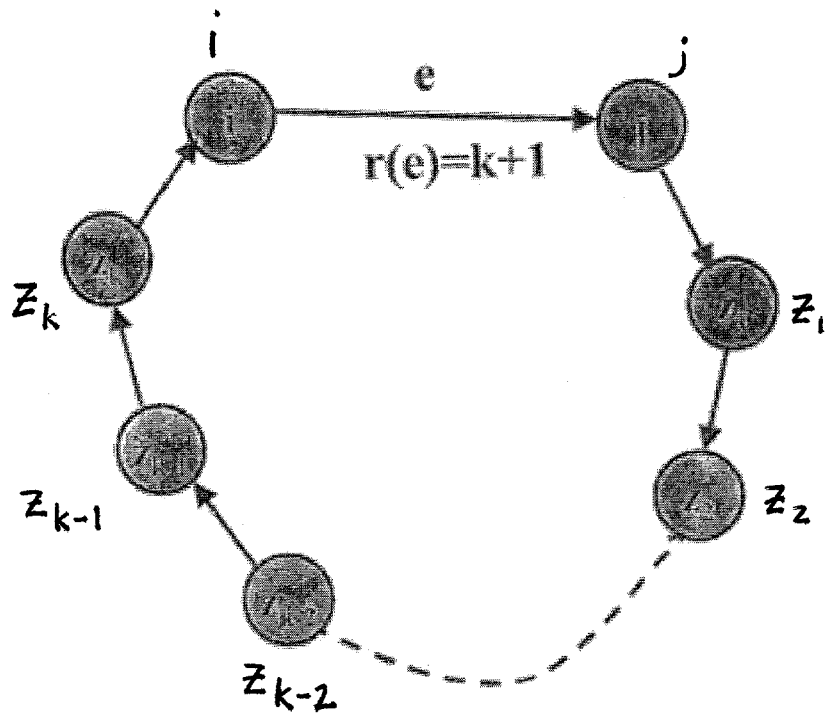
FIG. 8 illustrates a shortcut as an edge e connecting two nodes, i and j, that are also connected via a longer path of edges. The shortcut e shown here is a shortcut of range k+1. That is, when eliminating e, i and j are still connected by a path of length k+1.
FIG. 9 illustrates a recursive pruning algorithm to reconstruct the most parsimonious graph from an accessibility list.

A shortcut of range k+1 is illustrated in FIG. 8, wherein a shortcut is an edge e connecting two nodes, i and j, that are also connected via a longer path of edges. The shortcut e shown here is therefore a shortcut of range k+1 (i.e., a shortcut provides a shortest route between two nodes which are also connected by a longer path). That is, when eliminating e, i and j are still connected by a path of length k+1.

Lemma 1: For any accessibility list Acc of a digraph, there exists a compatible graph $G_{pars}$ that is free of shortcuts.

Proof: Assume there is no such graph $G_{pars}$. Without loss of generality, let G be a digraph inducing Acc. By assumption, G has a finite number of node pairs, $(x_1, y_1), \ldots, (x_n, y_n)$, each of which has the following property: There exists a directed edge $e_i$ from $x_i$ to $y_i$, as well as a path $P_i$ from $x_i$ to $y_i$ of length greater than 1. Take, without loss of generality, the first pair of such nodes, $(x_1, y_1)$, and generate from G a graph G* from which the edge $e_1$ is deleted. This graph has the same accessibility list as G, because $x_1$ and $y_1$ are still connected via $P_1$. By repeating this procedure with the remaining (n−1) node pairs, one arrives at a graph $G^{(n*)}$ with the same accessibility list as G but without shortcuts. This is a contradiction to the assumption made in the beginning of the proof.

Lemma 2: Assume that Acc is the accessibility list of a digraph G. For each node x, the adjacency list Adj(x) of a shortcut-free graph $G_{pars}$ compatible with Acc is a subset of the adjacency list Adj(x) of any graph compatible with Acc.

Proof: Assume that Lemma 2 is false. Consider then, without loss of generality, a shortcut-free graph $G_{pars}$ that induces Acc, and some other graph G that also induces Acc. By assumption, $G_{pars}$ contains at least one node x for which the following holds. Adj(x) of $G_{pars}$ contains at least one node y that is not in the adjacency list Adj(x) of G. But because G and $G_{pars}$ have the same accessibility list Acc, there must exist some path $x \rightarrow z_1 \rightarrow z_2 \rightarrow z_3 \rightarrow \ldots \rightarrow z_k \rightarrow y$ from x to y in G. Furthermore, because G and $G_{pars}$ have the same accessibility list, $z_1$ must be accessible from x in $G_{pars}$, $z_2$ from $z_1$ in $G_{pars}$ ... and $z_k$ from $z_{k-1}$ in $G_{pars}$. That means that we can find a path in $G_{pars}$, however indirect, that runs from x to $z_1$, from $z_1$ to $Z_2$, from $Z_2$ to $Z_3$, ... from $z_{k-1}$ to $z_k$, and from $z_k$ to y. But now we have two paths in $G_{pars}$, one of length one, the edge e between x and y, and one involving the nodes $z_1$ through $z_k$. Thus, the edge e (x→y) is a shortcut, in contradiction to the assumption that $G_{pars}$ is shortcut-free.

Corollary 1: The shortcut-free graph $G_{pars}$ compatible with Acc is a unique graph with the fewest edges among all graphs G compatible with Acc.

The corollary follows immediately from Lemma 2. A complementary way of showing that $G_{pars}$ is a minimal graph is to examine, first, the consequences of adding a node y to the adjacency list Adj(x) of some node x in $G_{pars}$. If y $\notin$ Acc(x) before the addition, now y $\in$ Acc(x), the accessibility list has changed, and the altered graph is no longer compatible with the original accessibility list. If, on the other hand, y$\in$ Acc(x) before the addition, then the addition has created a shortcut, so the graph is no longer shortcut-free. Second, what happens if you eliminate a node y from the adjacency list of any node x in $G_{pars}$? Then, y is no longer accessible from x, you have altered the accessibility list, and the resulting graph is no longer compatible with Acc. Assume that this was not so, that is, that y was still accessible from x. Then a path from x to y must have existed before the elimination of y from Adj(x). In that case, the edge from x to y was a shortcut, in contradiction to the assumption that $G_{pars}$ is shortcut-free.

The Algorithm

The network reconstruction algorithm takes the accessibility list Acc of an acyclic directed graph, and generates from it the adjacency list of the most parsimonious graph of Acc. It relies on two basic relations between accessibility and adjacency lists. The first is that for all nodes i a of a graph, Adj(i)$\subseteq$Acc(i). The second is formulated in the following Theorem.

Theorem 2: Let Acc(G) be the accessibility list of an acyclic directed graph, $G_{pars}$ its most parsimonious graph, and V($G_{pars}$) the set of all nodes of $G_{pars}$. Then the following identity holds.

$$\forall i \in V(G_{pars}) \; Adj(i) = Acc(i) \setminus \bigcup_{j \in Acc(i)} Acc(j) \qquad (1)$$

In words, for each node i the adjacency list Adj(i) of the most parsimonious genetic network is equal to the accessibility list Acc(i) after removal of all nodes that are accessible from any node in Acc(i).

Proof: The present inventor will first prove that every node in Adj(i) is also contained in the set defined by the right hand side of (1). Let x be a node in Adj(i). This node is also in Acc(i). Now take, without loss of generality any node j $\in$ Acc(i). Could x be in Acc(j)? If x could be in Acc(j) then we could construct a path from i to j to x. But because x is also in Adj(i), there is also an edge from i to x. This is a contradiction to $G_{pars}$ being shortcut-free. Thus, for no j $\in$ Acc(i) can x be in Acc(j). x is therefore also not an element of the union of all Acc(j) shown on the right-hand side of (1). Thus, subtracting this union from Acc(i) will not lead to the difference operator in (1) eliminating x from Acc(i). Thus x is contained in the set defined by the right-hand side of (1).

Every node in the set of the right-hand side of (1) is also in Adj(i). Let x be a node in the set of the right hand side of (1). Because x is in the right hand side of (1), x must a fortiori also be in Acc(i). That is, x is accessible from i. But x can not be accessible from any j that is accessible from i. For if it were, then x would also be in the union of all Acc(j).

Then taking the complement of Acc(i) and this union would eliminate x from the set in the right hand side of (1). In sum, x is accessible from i but not from any j accessible from i. Thus x must be adjacent to i.

The algorithm itself will use the following corollary to Theorem 2.

Corollary 2: Let i, j, and k be any three pairwise different nodes of an acyclic directed shortcut-free graph G. If j is accessible from i, then no node k accessible from j is adjacent to i.

Proof: Let j be a node accessible from node i. Assume that there is a node k accessible from j, such that k is adjacent to i. That is, $j \in Acc(i)$, $k \in Acc(j)$ and $k \in Adj(i)$. That k is accessible from j implies that there is a path of length at least one from j to k. For the same reason, there exists a path of length at least one connecting i to j. In sum, there must exist a path of length at least two from i to k. However, by assumption, there also exists a directed edge from i to k. Thus, the graph G cannot be short-cut free.

The algorithm itself takes the accessibility list of a graph and eliminates entries inconsistent with Theorem 2 and Corollary 2. It does so recursively until only the adjacency list of the shortcut-free graph is left. The algorithm is shown as pseudocode in FIG. 9. Because it operates on lists, programming languages such as perl or library extensions of other languages permitting list operations will facilitate its implementation. (Appendix B shows a perl implementation of the algorithm, where accessibility and adjacency list are represented by a two-dimensional hashing array.)

The algorithm (FIG. 9) needs an accessibility list for each node i, Acc(i), which would be obtained from gene perturbation data and subsequent gene activity measurements for a genetic network. In lines one and two (FIG. 9), for each node i the adjacency list Adj(i) is initialized as equal to the accessibility list. The algorithm will delete elements from this Adj(i) until the adjacency list of the most parsimonious network of Acc(G) is obtained.

The master loop in lines 3–6 cycles over all nodes of G, and calls the routine PRUNE_ACC for each node i. In the last statement of this routine (line 1) the calling node is declared as visited. Define a visited node as a node whose adjacency list Adj(i) needs not be modified any further. This is the purpose of the conditional statement in the master loop (line 4), which skips over nodes that have already been visited.

Aside from storing Acc and Adj, the algorithm thus also needs to keep track of all visited nodes. In an actual implementation, Acc, Adj, and any data structure that keeps track of visited nodes would need to be either global variables or passed into the routine PRUNE_ACC, preferably by reference. In contrast, the calling node i needs to be a local variable because of the recursivity of PRUNE_ACC.

The function PRUNE_ACC itself, which is the algorithm's core, is now explained. It contains of two loops. The first loop (lines 8–13) cycles over all nodes j accessible from the calling node i. If there exists a node accessible from j, then PRUNE_ACC is called from j. If no node is accessible from j, that is, if Acc(j)=∅, then j is declared as visited. Because its accessibility list is empty, its adjacency list must be empty as well (Adj(i)⊆Acc(i)), and needs no further modification. Thus, through the first loop PRUNE_ACC calls itself recursively until a node is reached whose accessibility list is empty. There always exists such a node, otherwise the graph would not be acyclic. This also means that infinite recursion is not possible for an acyclic graph. Thus, the algorithm always terminates. More precisely, the longest possible chain of nested calls of PRUNE_ACC is (n−1) if G has n nodes. For any node i calling PRUNE_ACC, the number of nested calls is at most equal to the length of the longest path starting at i.

The second loop of PRUNE_ACC (lines 14–18) only starts once the algorithm has explored all nodes accessible from the calling node i, that is, as the function calls made during the first loop return. In the second loop the principle of Corollary 2 is applied. Specifically, the second loop cycles over all nodes j accessible from i in line 14. In a slight deviation from what Corollary 2 suggests, line 15 cycles not over all nodes k∈Acc(j), but only over k∈Adj(j). All nodes k∈Adj(j) are deleted from Adj(i) in lines 16–18. Cycling only over k∈Adj(j) saves time, but does not compromise the requirement that all nodes k∉Adj(i) be removed, because line 14 covers all nodes j accessible from i. Because of the equality proven in Theorem 2, once this has been done, the adjacency list need not be modified further. This is why upon leaving this routine, the calling node is declared as visited. Notice also that if a node j with Acc(j)=∅ is encountered, the loop in line 15 is not executed.

Computational and Storage Complexity

Both measures of algorithmic complexity are influenced by the average number of entries in a node's accessibility list. Let k<n−1 be that number. For all practical purposes, there will be many fewer entries than that, not only because accessibility lists with nearly n entries are not accessibility lists of acyclic digraphs, but also because most real-world graphs are sparse.

During execution, each node accessible from a node j induces one recursive call of PRUNE_ACC, after which the node accessed from j is declared as visited. Thus, each entry of the accessibility list of a node is explored no more than once. However, line 15 of the algorithm (FIG. 9) loops over all nodes k adjacent to j. If a=|Adj(j)|, on average, then overall computational complexity becomes O(nka).

For practical matters, large scale experimental gene perturbations in the yeast *Saccharomyces cerevisiae* (n≈6300) suggests that k<50 a≦1 and thus that nka<<$n^2$ in that case. In practice, a network of 6,300 nodes (the approximate number of genes in the genome of the yeast *Saccharomyces cerevisiae*) and the same number of edges was reconstructed in approximately 15 seconds on a desktop workstation (450 MHz Pentium II; RedHat Linux 6.2), using the perl implementation of the algorithm shown in the Appendix B. Even for the much larger human genome (n≈30000), network reconstruction would thus be feasible on a desktop computer.

The system and method stores two copies of the accessibility list, as well as a list of the nodes that have been visited. The recursion stack requires additional storage. However, the recursion depth can be no greater than n−1 because otherwise the graph would not be acyclic. Thus, overall storage requirements are O(nk).

Each node of a directed graph lies in exactly one strong component. This holds also for acyclic graphs, if one defines that a graph (or the subgraph of G) with only one node is a strong component of G. The condensation G* of a directed graph G has the strong components of the graph G as its nodes,. Denote the components of G (nodes of G*) as $S_1, \ldots, S_k$. There is an edge from any $S_i$ to any $S_j$ in G* if there is an edge in G from at least one node in the component $S_i$ to at least one node in the component $S_j$. The relationship of a graph and its condensation is illustrated in FIGS. 10A–B. FIG. 10A shows a cyclic graph of 16 nodes. Upon close examination one finds one component with 5 genes (1,3,4,5,15; diamond-shaped nodes), another component with three genes (3, 6, 9; rectangular nodes), and eight remaining single-gene components (round nodes). FIG. 10B shows the condensation of the graph in FIG. 10A, where the two non-trivial components are now collapsed into single nodes. The condensation is an acyclic graph and can be reconstructed from the accessibility list.

To reconstruct a genetic network from single-gene perturbation experiments, one thus needs to identify all the strong components from experimental results, that is, from the accessibility list. The following theorem is very useful for doing that.

Theorem 3 Let P be the accessibility matrix of a digraph G with n nodes, $x_1, \ldots, x_n$. The strong component containing $x_i$ is determined by the unit entries of the i-th row in the matrix $P \times P^T$. (The superscripted 'T' denotes the matrix transpose of P, and the product 'x' is the element wise or Hadamard product of the two matrices.) See Harary, F., (1969) Graph theory. Addison-Wesley, Reading, Mass.

Corollary 3: Let i and j (i≠j) be two nodes of a digraph G. i and j are in the same component if i∈Acc(j) and if j∈Acc(i).

Figures 10, 11:
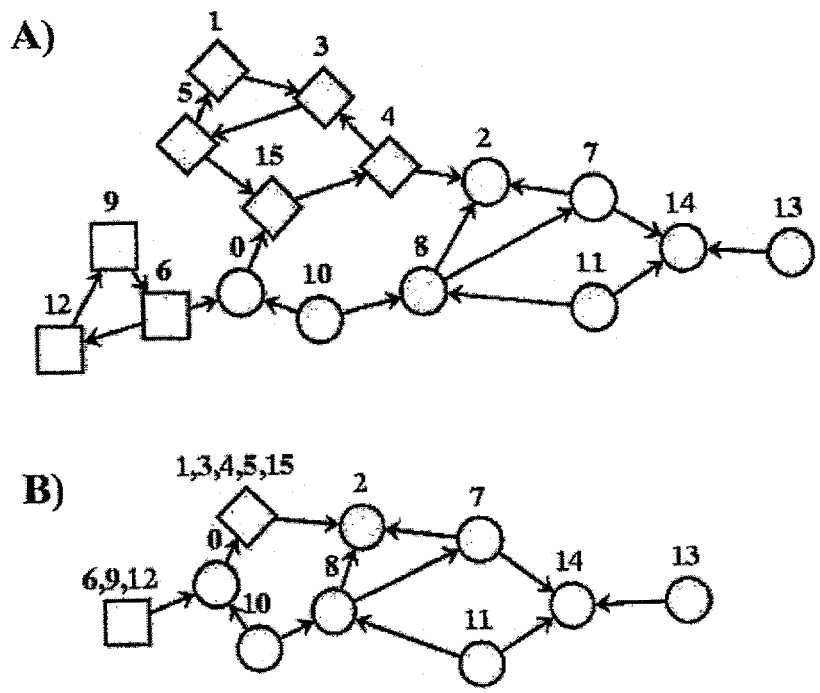
FIG. 11 illustrates one embodiment of an algorithm to calculate the condensation of a cyclic network from perturbation data.

An algorithm applying this corollary to identify the strong components of a graph from the accessibility list is shown in FIG. 11 as pseudocode. Not only does it identify the strong components, it also generates a new graph G*, the condensation of G. To this end, it uses a data structure component [i] which is an array indexed by the nodes i of G and pointing to a node of G* which corresponds to the component in which i resides. (In an actual implementation of the algorithm, a hashing array might be a convenient representation of such a data structure).

Before the algorithm starts, component [i] is undefined for all nodes i of G. The algorithm itself has two parts. In the first part (lines 1–9 in FIG. 11), it cycles through all nodes of G. If a node i is found that has not been mapped onto a component (line 2), that is, the component which i belongs to has not yet been defined, then a new node of G* is created (line 3), and i is mapped onto that node (line 4). Then, a loop (line 5) cycles over all nodes in Acc(i) and applies the above corollary to identify nodes in the same component as i. These nodes are then also mapped onto component [i] (lines 6–8). Notice that the conditional statement in line 2 saves potentially much execution time if the graph has few components. This is because it prevents scanning the accessibility list of i (lines 5–8) if component [i] has been defined previously during the master loop (line 1). For instance, in the extreme case of a graph with only one component, the statements in the interior of the loop would only be executed for the first node i of the graph.

The second part of the algorithm then generates the accessibility list of G* from that of G. It first initializes this list to the empty list for each node i of G* (lines 10–11). It then cycles through all nodes i of G (line 12), and through each node accessible from i, that is, through all j∈ Acc(i). If i and j are in different components, that is, if they map to different nodes of G*, the node in G* represented by component [j] must also be in the accessibility list of component [i]. If it has not been added to that list (line 15), it is added in line 16.

Because the graph G* has at most the same number of nodes and accessibilities as G, and because the algorithm generates only one copy of G* and its accessibility list, both storage and time complexity scale as O(k) where k is the number of entries of the accessibility list ($k < n^2$).

EXAMPLES

The following examples are presented by way of illustration of the previously described invention and are not limiting of that description.

The system and method of the present invention utilize the algorithms described herein to reconstruct both large and small genetic circuits. The algorithm presented here can be used to reconstruct a genetic network for an entire organism from perturbation data of all genes. At the time of this writing, more than 90% of all genes of the yeast *Saccharomyces cerevisiae* have been perturbed by targeted gene deletion. Similarly large-scale genetic perturbation projects are under way in the fruit fly *Drosophila melanogaster*, the nematode *Caenorhabditis elegans*, as well as in plants. In such experiments some genes are difficult to perturb, because they are essential to the organism. It is then also difficult to assess how their activity affects the activity of other genes. Sometimes a different kind of perturbation provides a solution to this problem, such as overexpression or conditional expression instead of gene deletion. Even so, it is likely that some genes remain impossible to perturb, or that one cannot measure their perturbation effect. In the reconstruction of smaller genetic networks one encounters similar problems. For example, one might be interested in the regulatory interactions of all genes required for sporulation, or for chromosome segregation, or for the repair of radiation damage. Through earlier experiments, one might have an idea about what these genes are. For instance, one might have carried out a saturation mutagenesis experiment, or a large-scale gene expression study monitoring all genes whose expression changed during the process in question. However, some genes involved in the process of interest may not have been detected by this approach.

Thus when reconstructing a genetic network the issue of missing information or genes for which no perturbation data is available does occur. The system and method of the present invention addresses this issue by restricting analysis to acyclic networks. The reason is that eliminating expression information from a cyclic network may change the number of cycles observed, and thus the number of nodes in the network's condensation.

To assess robustness of the algorithm from FIG. 9 to missing genes, a random graph of a pre-specified number of nodes and edges is generated. The graph is then rendered acyclic by removal of suitably chosen edges. Random networks are used purely for reasons of computational convenience. However, analyses of the structure of large-scale metabolic and genetic networks suggest that these networks share important features with random networks. For both types of networks, information is eliminated on a pre-specified fraction of its nodes from its accessibility list in the following way. For each of the nodes X, eliminate all entries of Acc(X) as well as all entries of X found in the accessibility lists of other genes. Reconstructing a network from this modified accessibility list using the algorithm of FIG. 9, it is possible to determine what fraction of edges remaining between the existing nodes that the algorithm has identified correctly.

Figure 12:
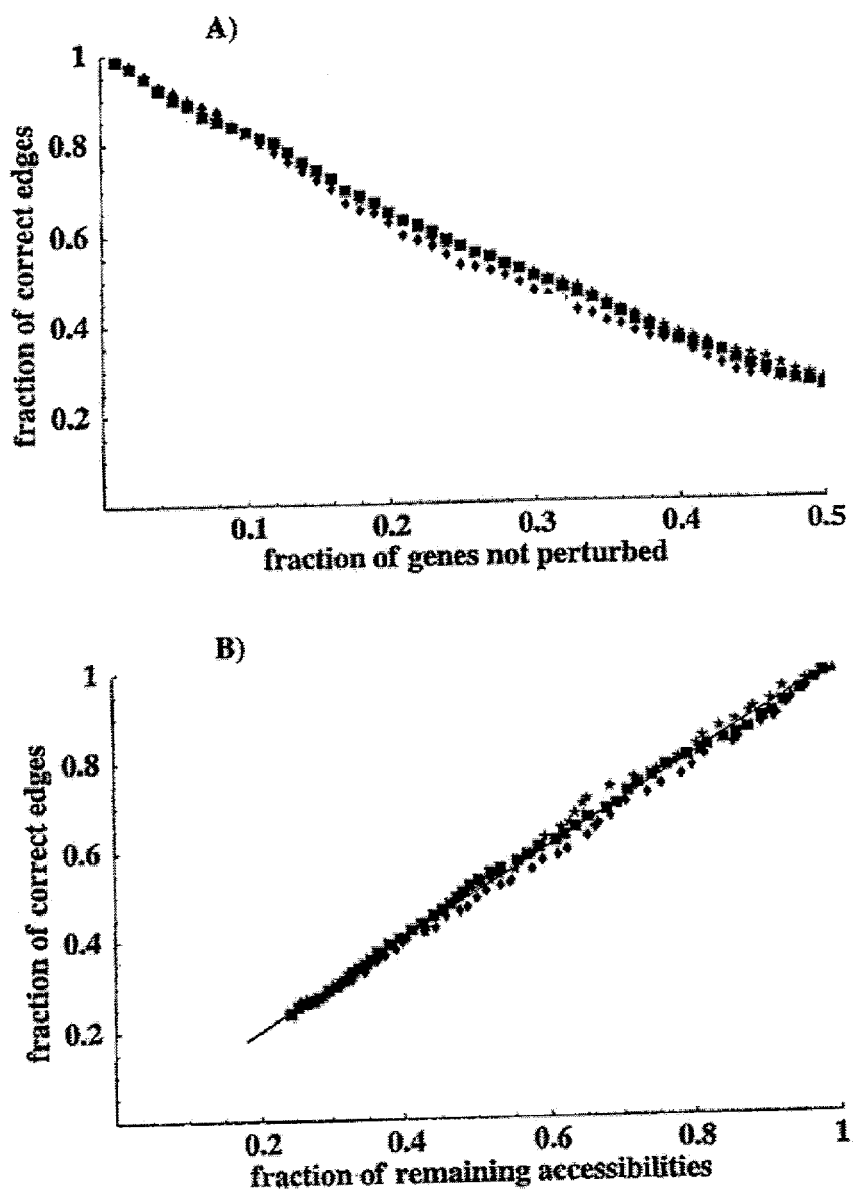
FIG. 12 illustrates results for three random graphs of 500 nodes and 250 edges (diamonds), 500 edges (stars), or 750 edges (squares), from which edges are removed until each network is rendered acyclic.

The results are shown in FIGS. 12A–B for three random networks of 500 nodes and 250 edges (diamonds), 500 edges (stars), or 750 edges (squares), from which edges are removed until each network is rendered acyclic. After removal of these edges, the resulting three acyclic graphs have 250, 492, and 646 edges, respectively. The pruning algorithm is then applied to the accessibility list of each of these networks, as well as to the same accessibility list after information on a pre-specified number of nodes is removed, as explained in the main text. This reduced accessibility list emulates a situation where a number of genes have not been perturbed. FIG. 12A shows on the abscissa a measure of the number of these genes, that is, the fraction of genes on which information is missing. Plotted against it is the fraction of correctly reconstructed edges. More precisely, it is the fraction of edges that the network reconstructed with missing perturbation information has in common with the network with complete information. FIG. 12B shows the same measure of reconstruction quality. The only difference to FIG. 12A is that the abscissa shows the fraction of remaining entries of the accessibility list, and not the fraction of missing genes. The value of one on the abscissa refers to the number of entries of the accessibility list for a network where all genes were perturbed. As the fraction of missing genes increases from 0 to 0.5 (as shown in A), the fraction of remaining entries of the accessibility list decreases from one to approximately 0.25 for all three networks shown. Both panels show that the quality of network reconstruction is not very sensitive to the number of edges in the network. The most direct predictor of this quality is the number of remaining entries of the accessibility list. This is indicated by the slope of the regression line shown in B) through the data points pooled for all three networks. It is nearly identical to one ($y=1.01x-0.002$; Pearson $r^2=0.994$).

Quality of network reconstruction is not sensitive to the number of edges, but decays linearly with the number of genes on which information is missing (FIG. 12A). The best predictor of the quality of reconstructed networks is the fraction of entries of the accessibility list remaining after removal of a certain fraction of nodes. Its relation to the fraction of correctly reconstructed direct interactions is practically one to one, as indicated by the slope of the regression line in FIG. 12B. This is not surprising, as one can think of each accessibility as a bit of information used in reconstructing the network. It would in fact be very surprising if the reconstruction algorithm could do any better than shown in FIG. 12B, that is, if the slope of the regression line could be much less than one. This would mean that for any entry removed from an accessibility list removed, one would lose less than one accurately reconstructed direct interaction. Conversely, a slope much greater than one would indicate poor performance, in the sense that the algorithm does not use all information contained in an accessibility list.

Another problem, as discussed above, is flawed data (i.e., spurious or missing entries of an accessibility list). Such data is the result of errors in measuring gene activities. As stated earlier, the reason why flawed data is a problem is that not just any list of the form shown in FIG. 1C is the accessibility list of a graph. Taking the accessibility of the simple network 1→2→3 and eliminating only one entry, as indicated in parentheses:

| 1: | 2 | (3) |
|---|---|---|
| 2: | 3 | |
| 3: | | | results in a list that is not the accessibility list of a graph anymore. Again, one can be convinced that even for simple graphs, removal or addition of entries can lead to arbitrarily pathological situations, such as structures that look like cycles in the accessibility list but that do not correspond to any possible cycle in a graph. As before, such pathologies may pose challenges for any reconstruction algorithm.

As addressed above, there are two ways to address this problem. One way is to use only the most reliable data. For example, in a micro array experiment assessing the effect of a gene deletion on the mRNA expression state of other genes, some genes change expression to a greater extent than others. One could only use those genes whose expression state has changed beyond a pre-specified threshold, according to some suitable statistical criterion. However, being excessively conservative leads to failure to identify some important interactions.

The second way regards heuristic modifications to the algorithm. For example, because no cycle in a graph of n nodes can be longer than n edges, one might set a limit to the recursion depth of the algorithm to prevent infinite recursion in case an accessibility list contains spurious cycles. If that recursion depth is exceeded for at least one node, the algorithm (FIG. 11) generating the condensation is applied repeatedly, until the pruning algorithm (FIG. 9) yields an adjacency list. Even with such heuristic modifications, it is almost certain that one can arbitrarily construct pathological "accessibility" lists for which any algorithmic modification would yield little or no useful information on the network. Modification of the algorithm depends on error structure of the empirical data. The error structure may depend on gene activity and the kind of perturbation used. As large-scale genetic perturbation data is accumulating, the statistical nature of these errors will become clear.

Figure 13:
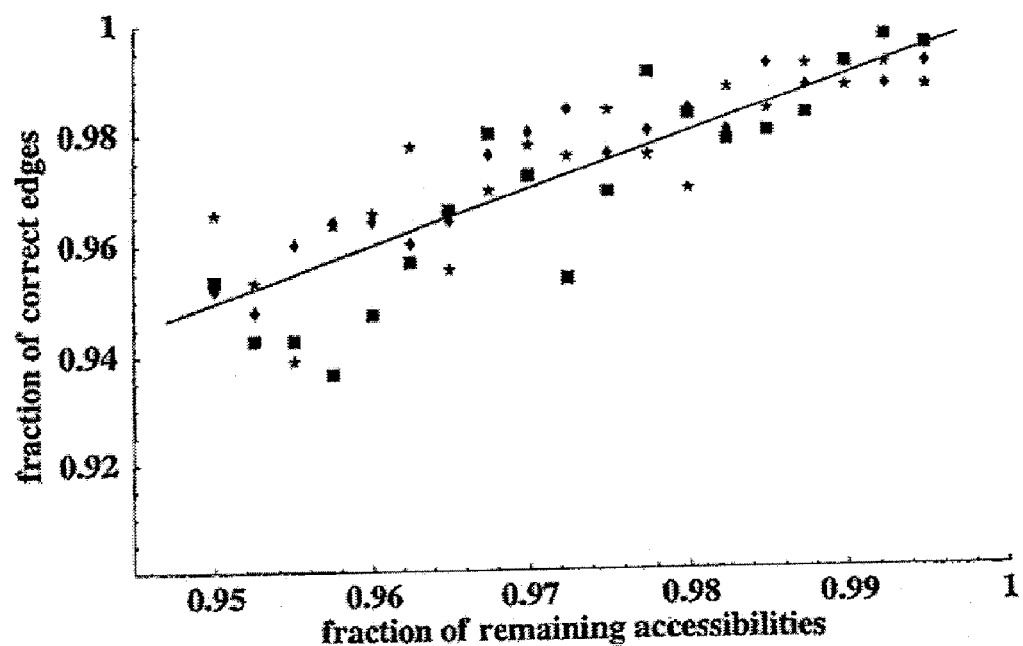
FIG. 13 illustrates results for three random graphs of 500 nodes and 250 edges (diamonds), 500 edges (stars), or 750 edges (squares).

One assessment of algorithmic robustness to defects in the accessibility list is dependent upon the robustness of the algorithm to missing entries of the accessibility list. Current techniques to measure the effects of gene perturbations on gene activity, such as transcriptional activity measurements provided by micro arrays, are very noisy. Therefore, only gene perturbation data from genes whose expression level changes by more than some pre-specified factor are included. This factor is chosen in a statistically conservative way in order to avoid false positives results. A statistical conservative factor leads to the problem that some genes actually affected by the perturbation are not identified as affected. The fraction of perturbed genes excluded by the factor can be identified through experimentation. An example of such an experiment might include: generating a random network of a pre-specified number of nodes and edges along with its accessibility list, and eliminating a fraction of the entries of its accessibility list at random. Then apply the algorithm from FIG. 9 to the list thus generated, and assess the fraction of edges that the algorithm identifies correctly, that is, the fraction of edges that are in both the actual network and the network reconstructed from the changed accessibility list. FIG. 13 shows the results of this analysis. Very similar to what has been shown in FIG. 12, and for the same reasons, the quality of network reconstruction shows a statistical one-to-one relationship with the number of remaining entries of the accessibility list.

Results are shown in FIG. 13 for three random graphs of 500 nodes and 250 edges (diamonds), 500 edges (stars), or 750 edges (squares), from which edges are removed until each network is rendered acyclic. After removal of these edges, the resulting three acyclic graphs have 250, 492, and 646 edges left, respectively. For each of these networks, a pre-specified fraction of entries is then eliminated at random from the accessibility list. The fraction of remaining entries is shown on the abscissa. The pruning algorithm is applied to the changed accessibility list, and the network it reconstructs is then compared to the actual graph. More precisely, the fraction of correctly identified edges in the reconstructed network with missing accessibilities is determined. This fraction is shown on the ordinate axis. There is a statistical one-to-one relation between the number of remaining entries and the fraction of correctly reconstructed interactions (y=1.006×−0.006; Pearson $r^2$=0.75).

The present invention will answer a multitude of questions about the genetic architecture of organisms such as 1) identifying the structure of genetic networks, 2) identifying how patterns of gene interactions change in different developmental stages, in different physiological states, in different environmental conditions, or in different cell types, 3) identifying genes that are master regulators, i.e., genes that drive large parts of a physiological or developmental machinery, 4) determining whether the master regulators have a characteristic profile of regulatory interactions. The present invention can help sift through a large amount of genomic information to identify candidate genes for targeted biochemical investigation. The present invention as a tool to identify direct gene interactions has broad applications in basic and applied biomedical research. To give but two examples, it may be useful to identify targets for conventional therapeutic agents or for gene therapy. Second, there may be variation in genetic network structure within human populations. If so, the tool can be used to identify the nature of this variation, and thus provide information useful to pharmacogeneticists.

There are also countless applications to organisms other than humans. One example is agricultural biotechnology, where the design of effective pesticides may depend on our understanding of gene interactions involved in host defense, pest survival, reproduction, or virulence. In sum, a tool to reconstruct genetic network structure from gene perturbation data is useful wherever regulatory gene interactions are important for our understanding of how organisms, be they humans, animals or plants, function, or how disease comes about.

Alternate Embodiments

In an alternate embodiment, it can be useful to determine the longest path connecting two genes, such as for comparison to other paths or to use to determine the path that is most likely to be interrupted.

The longest path algorithm presented herein rests on the following two propositions.

Proposition 1. For two nodes u and w of an acyclic, shortcut-free digraph, let p(u,w) be the length (number of edges) of a longest path connecting u and w (p(u,u)=0, p(u,w)=∞ if $$\forall w \in Acc(u): p(u, w) = \max_{\{v | v \in Acc(u) \wedge w \in Acc(v)\}} p(u, v) + p(v, w)$$

$$w \notin Acc(u)).$$

That is, the longest path p(u,w) between u and w, where w is accessible but not adjacent to u, is equivalent to the sum over the longest paths p(u,v)+p(v,w), maximized over all v from which w is accessible. The Proposition is a consequence of path length additivity in a graph. If w is adjacent to u, then v=u, and p(u,w)=p(u,u)+p(u,w)=0+1=1. No path with p(u,w)>1 exists in this case, because the graph is shortcut-free.

The following could be viewed as a special case of Proposition 1.

Proposition 2: For two nodes u and v of an acyclic, shortcut-free digraph, let p(u,v) be the length (number of edges) of a longest path connecting u and v (p(u,u)=0, p(u,v)=∞ if v∈Acc(u)).

$$\forall w \in Acc(u) \setminus Adj(u): p(u, w) = \max_{\{v | v \in Acc(u) \wedge w \in Acc(v)\}} 1 + p(v, w)$$

Proof: For the purpose of this proof, consider only nodes v from the set {v|v∈Acc(u)∧ w∈Acc(v)} Among such nodes v, the present inventor will distinguish between those adjacent to u, and those accessible but not adjacent to u. For any v∈Adj(u), p(u,v)=1 because the graph is shortcut-free. A longest path (not necessarily unique) from u to w must pass through one $v_i$∈Adj(u). The length of this longest path is one plus the length of the longest path from $v_i$ to w. Thus, to arrive at a longest path between u and w, one can take the above maximum over v∈Adj(u). What remains to be shown is that there exists no $v_j$ accessible but not adjacent to u ($v_j$∈Acc(u)\Adj(u)) so that $$1 + p(v_j, w) > \max_{\{v | v \in Adj(u) \wedge w \in Acc(v)\}} 1 + p(v, w) = p(u, w)$$

Assume there was such a $v_j$∈Acc(u)\Adj(u). Because $v_j$ is accessible from u, there exists a $v_h$ adjacent to u, such that the longest path from u to $v_j$ is given by p(u,$v_j$)=1+p($v_h$,$v_j$). Because of Proposition 1, p(u,w)≧p(u,$v_j$)+p($v_j$,w), and in sum we have p(u,w)≧p(u,$v_j$)+p($v_j$,w)=1+p($v_h$,$v_j$)+p($v_j$,w)> 1+p($v_j$,w), which is in contradiction to the assumption.

Proposition 2 does not apply to nodes w∈Adj(u), but for those nodes p(u,w)=1. One might surmise that an exactly analogous proposition must hold for minimum path lengths $p_{min}$(u,w). That is not the case. The reason lies in the second half of the proof. For u,w such that $p_{min}$(u,w)>2, there exists a $v_j$∈Acc(u)\Adj(u), such that 1+$p_{min}$($v_j$,w)<$p_{min}$(u,w). It is a $v_j$ adjacent to w, for which $p_{min}$($v_j$,w)=1. (However, minimum path lengths can easily be reconstructed from a breadth first search on the adjacency list Acc(u), given by all v such that p(u,v)=1.)

The Maximum Path Algorithm

The recursive algorithm shown as pseudocode in FIG. 3 takes advantage of Proposition 2 to build a list of maximum path lengths p(u,v) in a graph. Because it operates on lists, programming languages such as perl or library extensions of other languages permitting list operations will facilitate its implementation. (Appendix A shows a perl implementation of the algorithm, where accessibilities and path lengths are represented by a two-dimensional hashing array.)

The algorithm (FIG. 3) needs an accessibility list for each node u, Acc(u), which would be obtained experimentally from gene perturbation data and subsequent gene activity measurements. Initially all pathlengths p(u,v) should be undefined or assigned some impossibly small value, such as p(u,v)=−1. In lines one through four (FIG. 3), a master loop cycles over all nodes u and calls the routine MAXPATH for each node u. In the last statement of this routine (line 17) the calling node is declared as visited. Once a node u has been visited, the maximum path lengths p(u,v) to all v∈Acc(u) have been calculated. The conditional statement in the master loop (line 2) skips nodes that have already been visited.

Aside from storing Acc and path lengths, the algorithm needs to keep track of all visited nodes. In an actual implementation, Acc, path lengths, and any data structure that keeps track of visited nodes must be either global variables or passed into the routine MAXPATH, preferably by reference. In contrast, the calling node u needs to be a local variable because MAXPATH is recursive.

The function MAXPATH itself will now be explained, which is at the algorithm's core. It consists of two loops. The first loop (lines 6–12) cycles over all nodes v accessible from the calling node u. If there exists a node accessible from v, then MAXPATH is called from v. If no node is accessible from v, that is, if Acc(v)=Ø, then v is declared as visited. Because its accessibility list is empty in this case, there exists no node z for which p(v, z) has a positive integer value. Thus p(v, z) needs no further modification. In sum, MAXPATH calls itself recursively in the first loop until a node is reached whose accessibility list is empty. There always exists such a node, otherwise the graph would not be acyclic. This also means that infinite recursion is not possible for an acyclic graph. Thus, the algorithm always terminates. More precisely, the longest possible chain of nested calls of MAXPATH is (n−1) if G has n nodes. For any node u calling MAXPATH, the number of nested calls is at most equal to the length of the longest path starting at u.

In line 12, the last statement of the first loop, the longest path from u to v is temporarily assigned a length of one, which is the smallest possible maximum path length for any v∈Acc(u).

This assignment is the departure point for the iterative path length calculations in the second loop of MAXPATH (lines 13–15), where Proposition 2 is applied to determine p(u,v) for each v accessible from u. This loop only starts once the algorithm has explored all nodes accessible from the calling node u, that is, as the function calls made during the first loop return. The iteration scheme in lines 13 and 14 deserves some explanation. Following Proposition 2, one would first iterate over all nodes w∈Acc(u), and then maximize 1+p(v,w) over all v with w∈Acc(v). This would require, for each v, a time consuming search to determine whether w∈Acc(v). Instead, the algorithm uses a modified iteration scheme, which essentially swaps the order of iterations. It iterates first over all nodes v∈Acc(u), and then over all w∈Acc(v) to maximize 1+p(v,w) (line 15). By the time line 15 of the second loop is reached, all nodes v accessible from u have been visited in previous calls to MAXPATH. Thus, all p(v,w) are known, which is what the calculation of p(u,w) relies on. In sum, lines 13–15 determine all p(u,w), except for nodes adjacent to u, for which the maximum path lengths is one (established on line 12), and u itself, for which p(u,u)=0 (line 16).

A by-product of the algorithm is the adjacency list of each node U, that is, the list of nodes v for which p(u,v)=1. From this list, minimum path lengths can easily be reconstructed using a breadth-first search algorithm. There are other recursive methods that may be used to calculate the adjacency list. It will be clear to those of ordinary skill in the art what those are. The present invention discloses two recursive algorithms that are the preferred embodiment.

Computational and Storage Complexity

Both measures of algorithmic complexity are determined by the average number of entries in a node's accessibility list. Let k<n−1 be that number. For all practical purposes, there will be many fewer entries than that, not only because accessibility lists with nearly n entries are not accessibility lists of acyclic digraphs, but also because most real-world graphs are sparse.

During execution, each node v accessible from a node u induces one recursive call of MAXPATH, after which the node accessed from u is declared as visited. Thus, each entry of the accessibility list of a node is explored no more than once. However, line 14 of the algorithm (FIG. 3) loops over all nodes w accessible from the called node v. This leads to overall computational complexity $O(nk^2)$.

For practical matters, large scale experimental gene perturbations in the yeast *Saccharomyces cerevisiae* (n≈6300) suggests that k<50 and thus that $nk^2<n^2$ in that case. In practice, a network of 6,300 nodes (the approximate number of genes in the genome of the yeast *Saccharomyces cerevisiae*) and the same number of edges was reconstructed in less than 30 seconds on a desktop workstation (450 MHz Pentium II; RedHat Linux 6.2), using the perl implementation of the algorithm shown in Appendix A. Even for the much larger human genome (n≈30000), network reconstruction would thus be feasible on a desktop computer.

In terms of memory requirements, the algorithm needs a copy of the accessibility list (O(nk)), a list of path lengths (O(nk)), as well as a list of the nodes that have been visited (O(n)). The recursion stack requires additional storage. However, the recursion depth can be no greater than n−1 because otherwise the graph would not be acyclic. Thus, overall storage requirements are O(nk).

Messy Data

Any gene perturbation experiment will be subject to measurement error. Either genes affected by a perturbation will not be detected as such, or genes unaffected will show spurious changes in activity. This will affect the accessibility list generated by an experiment, which is a problem, because not just any list of the form shown in FIG. 1C is the accessibility list of a graph. Take the accessibility list of the simple graph 1→2→3. Eliminate only one entry, indicated in parentheses

| 1: | 2 | (3) |
|---|---|---|
| 2: | 3 | |
| 3: | | | and the resulting list is not the accessibility list of a graph anymore. One can be convinced that even for simple graphs, removal or addition of entries can lead to arbitrarily pathological situations, such as structures that look like cycles in the accessibility list but that do not correspond to any possible cycle in a graph. Such pathologies pose challenges for any reconstruction algorithm.

There are two approaches to address this problem. One approach is to use only the most reliable data. For example, in a micro array experiment assessing the effect of a gene deletion on the mRNA expression state of other genes, some genes change expression to a greater extent than others. One could only use those genes whose expression state has changed beyond a pre-specified threshold, according to some suitable statistical criterion. However, being excessively conservative would lead to failure to identify some important interactions.

The second approach regards heuristic modifications to the algorithm. For example, because no cycle in a graph of n nodes can be longer than n edges, one might set a limit to the recursion depth of the algorithm to prevent infinite recursion in case an accessibility list contains spurious cycles. If that recursion depth is exceeded for at least one node, one can generate the graph's condensation iteratively, until the reconstruction algorithm (FIG. 3) yields an adjacency list. Even with such heuristic modifications, however, it is almost certain that one can construct arbitrarily pathological "accessibility" lists for which any heuristic modification would fail. If and how the algorithm should be modified depends on the error structure of the empirical data. This error structure, in turn, may depend on the notion of gene activity and also on the kind of perturbation used. As large-scale genetic perturbation data is accumulating, the statistical nature of these errors will become clear.

To provide a crude assessment of algorithmic robustness to defects in an accessibility list, the present inventor analyzed robustness of the algorithm in FIG. 3 to missing and to added entries this list. This was done by (i) generating a random network of a pre-specified number of nodes and edges along with its accessibility list, and (ii) eliminating or adding a fraction of nodes to the accessibility list at random. The algorithm from FIG. 3 was applied to the list thus generated and determined the number of edges, corresponding to node pairs u,v, with p(u,v)=1, that the algorithm identifies correctly. More specifically, the fraction $f_-$ of edges in $G_{pars}$ that the algorithm does not identify as such (false negative edges) was determined, and the fraction of edges $f_+$ the algorithm finds but that are not part of $G_{pars}$ (false positive edges) was determined.

Figure 5:
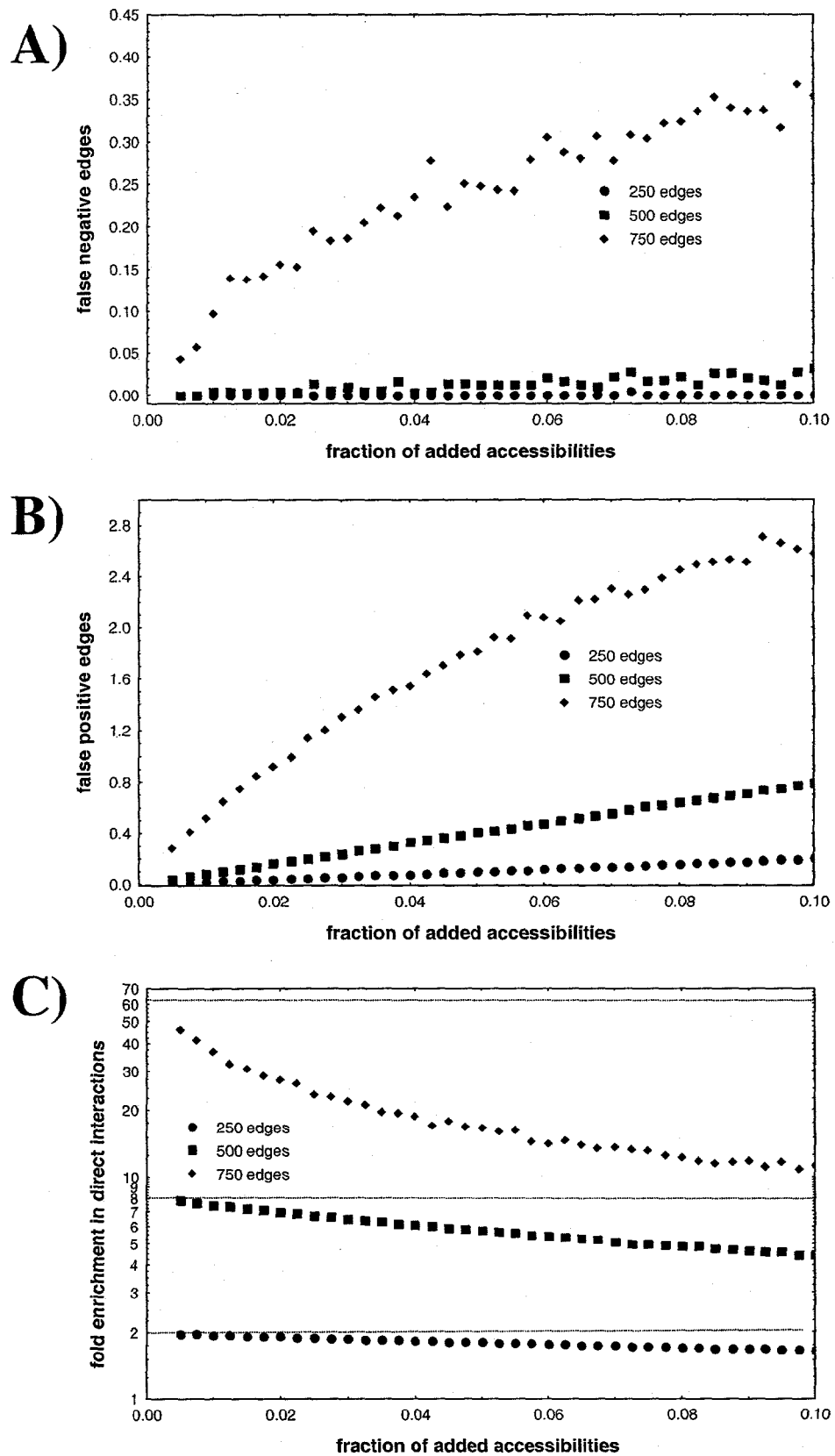
FIGS. 5A–C illustrates the quality of network reconstruction with spurious perturbation effects.

A complementary way of viewing algorithmic robustness is to analyze how much the algorithm "enriches" direct interactions in a reconstructed adjacency list. Let C be the number of entries in the accessibility list of a graph, and A the number of entries in the adjacency list. Then, a fraction A/C of entries in the accessibility list corresponds to direct regulatory interactions in Acc. One can think of A/C metaphorically as the "concentration" of direct interactions among all detected interactions. For instance, for the graph in FIG. 5 with 610 edges, there are 37889 entries of the accessibility list. Thus, only 610/37889, or about one $62^{nd}$ of all entries are direct interactions. Perfect network reconstruction would enrich direct interactions by a factor 62. With flawed data, the algorithm may not identify all direct interactions, but the adjacency list it produces may still be enriched for direct interactions. The quantity $$A(1-f_-)/A(1+f_+)=(1-f_-)/(1+f_+)$$

is the ratio of correctly identified direct interactions, $A(1-f_-)$, to the sum of the total number of entries of Adj and the number of false positive interactions, $Af_+$. It is at most one, in the case of perfect network reconstruction. As a measure for how much an algorithm enriches for direct interactions, the present inventor defines $$E=(C(1-f_-))/(A(1+f_+))$$

E attains its maximally possible value, C/A, for perfect network reconstruction. An E of 10 means that the "concentration" of direct interactions in a reconstructed adjacency list is 10 times greater than in the accessibility list of the same network.

Figure 4:
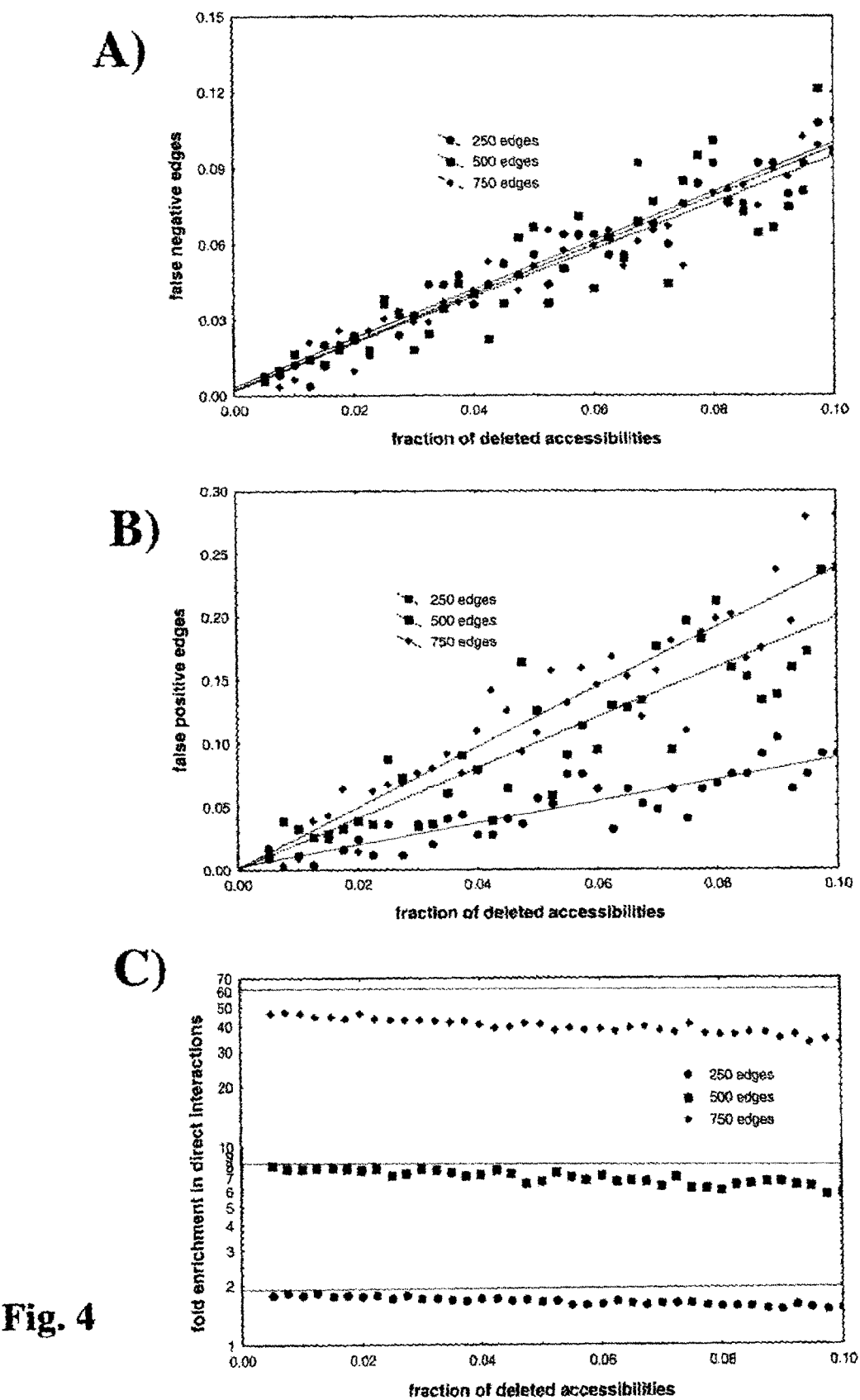
FIGS. 4A–C illustrate the quality of network reconstruction with unidentified perturbation effects.

FIGS. 4A–C illustrate the quality of network reconstruction with unidentified perturbation effects. Results are shown for three random graphs of 500 nodes and 250 edges (circles), 500 edges (squares), or 750 edges (diamonds), from which edges are removed until each graph is rendered acyclic. After removal of these edges, the resulting three acyclic graphs have 250, 494 and 624 edges left, respectively. For each of these networks, a pre-specified fraction of entries was then eliminated at random from the accessibility list. The fraction of remaining entries is shown on the abscissa of each panel. The algorithm from FIG. 3 was then applied to the changed accessibility list, and the resulting adjacency list was then compared to that of the maximally parsimonious graph of the original accessibility list. For the reconstructed network, FIG. 4A shows the fraction of false negative edges, FIG. 4B shows the fraction of false positive edges, and FIG. 4C shows by how many fold direct interactions are enriched (see text) in the reconstructed adjacency list, relative to the original accessibility list. A logarithmic scale is chosen in FIG. 4C merely to fit all data points conveniently on one graph. The dotted horizontal lines indicate the maximally possible enrichment, that is, for perfect network reconstruction.

FIGS. 5A–C illustrate the quality of network reconstruction with spurious perturbation effects. Results are shown for three random graphs of 500 nodes and 250 edges (circles), 500 edges (squares), or 750 edges (diamonds), from which edges are removed until each network is rendered acyclic. After removal of these edges, the resulting three acyclic graphs have 250, 494 and 610 edges left, respectively. For each of these networks, a pre-specified fraction of entries was then added at random to the accessibility list. For each added entry u, it was verified whether adding u as an edge would create a cycle in the graph. If so, a new u was chosen at random, until one was found that did not create a cycle. The fraction of entries thus added is shown on the abscissa of each panel. The algorithm from FIG. 3 was then applied to the changed accessibility list, and the resulting adjacency list was then compared to that of the maximally parsimonious graph of the original accessibility list. For the reconstructed network, FIG. 5A shows the fraction of false negative edges, FIG. 5B shows the fraction of false positive edges, and FIG. 5C shows by how many fold direct interactions are enriched (see text) in the reconstructed adjacency list, relative to the original accessibility list. As before with FIG. 4C, a logarithmic scale is chosen in FIG. 5C merely to fit all data points conveniently on one graph. The dotted horizontal lines indicate the maximally possible enrichment, that is, for perfect network reconstruction.

As such, FIGS. 4A–C and 5A–C illustrate the robustness of the algorithm to deleted and added accessibilities, respectively. The algorithm generates fewer false negative than false positive edges for a given fraction of deleted (FIGS. 4A vs. 4B) or added (FIGS. 5A vs. 5B) accessibilities. Second, the algorithm is in general more sensitive to added accessibilities, in that both $f_-$ (4A vs. 5A) and $f_+$ (4B vs. 4C) are greater if the same fraction of edges is added as opposed to deleted. Third, $f_+$ depends more strongly on the interaction density in the network than $f_-$. An accessibility list derived from large scale gene perturbations in yeast suggests that transcriptional regulatory networks may be sparsely connected. That is, their edge density may fall between the two more sparsely connected graphs analyzed here. If true in general, this would be reassuring, because the lower the edge density in a graph, the greater the robustness of the algorithm.

The relation of E to the fraction of deleted and added entries of an accessibility list is shown in FIGS. 4C and 5C. Take the above example with 37889 entries of the accessibility list. For perfect network reconstruction (dotted line in FIGS. 4C and 5C), E≈62. If the size of the accessibility list is decreased or increased by 10%, the fractions of direct interactions in the reconstructed adjacency list are still 30-fold and 10-fold greater, respectively, than in the original accessibility list (FIG. 5C). Thus, even for substantially flawed data, leading to a sizable fraction of false negative and false positive edges, the algorithm may still significantly enrich direct interactions.

Genetic Network Complexity

In yet another aspect of the present invention, it is often useful to determine the complexity of a genetic network, such as for comparing alternate drug therapies. Complexity determination showing sparse networks is also helpful in analogizing the applicability and scalability of genetic graphs produced by the present invention for the yeast *Saccharomyces cerevisiae* to organisms with more genes, such as humans.

A graph-based approach is used to estimate coarse gene network structures from large scale gene perturbation data. The approach estimates the number of direct regulatory interactions in a network from the number of genes whose activity is affected by genetic perturbations. Applied to the results of a large-scale gene knockout experiment in the yeast *Saccharomyces cerevisiae*, the results suggests that the yeast transcriptional regulatory network is very sparse, containing no more direct regulatory interactions than genes. The network comprises more than one hundred independent sub-networks.

Given information like that in FIG. 1C, can one say anything about the structure of the network as defined in FIGS. 1A and 1B? The answer is yes, if one is willing to make assumptions about coarse statistical features of a genetic network. (Any large genetic network has such features, the question is just what they are.) In the absence of other information, the most parsimonious assumption would be that of a graph with a given number of edges, where any two nodes are equally likely to be connected by an edge. Such graphs are known as Erdös-Rényi (ER) random graphs. Recent analyses on cellular circuits as diverse as metabolic networks and a microbial protein interaction network show that these cellular networks share commonalities with ER random graphs, such as their short path lengths. However, a conspicuous deviation regards the distribution of the number of direct interactions per node in these networks. In the ER model, this number follows a Poisson distribution. However, in the studied cellular networks this number follows a broad-tailed power law distribution, where the likelihood that a randomly chosen node from the network has d direct interactions is $P(d) \propto d^{-\tau}$ ($1.5 < \tau < 2.5$). Such networks have not only a wider range of direct interactions per node, they also have a greater number of nodes with many direct interactions than ER networks. For transcriptional regulation networks (where gene perturbations influence mRNA gene expression patterns) such broad-tailed distributions meet an important biological objection to the ER model. It is that regulatory networks should consist of regulatory genes, genes that directly influence the activity of many genes, and other genes that influence the activity of few or no genes.

Further Examples

Using both the ER assumption and that of a broad-tailed distribution of direct regulatory interactions, one can coarsely estimate the number of direct interactions in a transcriptional regulation network. The ER model is included because it provides an upper bound for the number of direct interactions (see below). The data for the estimate come from a recent large-scale gene perturbation experiment in the yeast *Saccharomyces cerevisiae*, in which 271 yeast genes were deleted. The present inventor assessed the effect of each deletion on the mRNA expression level of 6312 yeast genes on synthetic complete medium (SC) using cDNA micro arrays. More specifically, for each genetic perturbation and for each of 6312 genes, they determined a ratio r=w/d of the relative expression level of a gene in the wild-type, w, and after a gene deletion, d. As micro array gene expression measurements are notoriously noisy, it is not clear what ratio R assures that a gene's expression has changed significantly relative to the wild-type. It is thus necessary to choose a threshold R beyond which an expression ratio is deemed significant. In the absence of rigorous statistical methods to determine an appropriate R, the present inventor will allow R to range between two (least conservative) and five (most conservative), and only results unaffected by changing R are reported.

Figure 14:
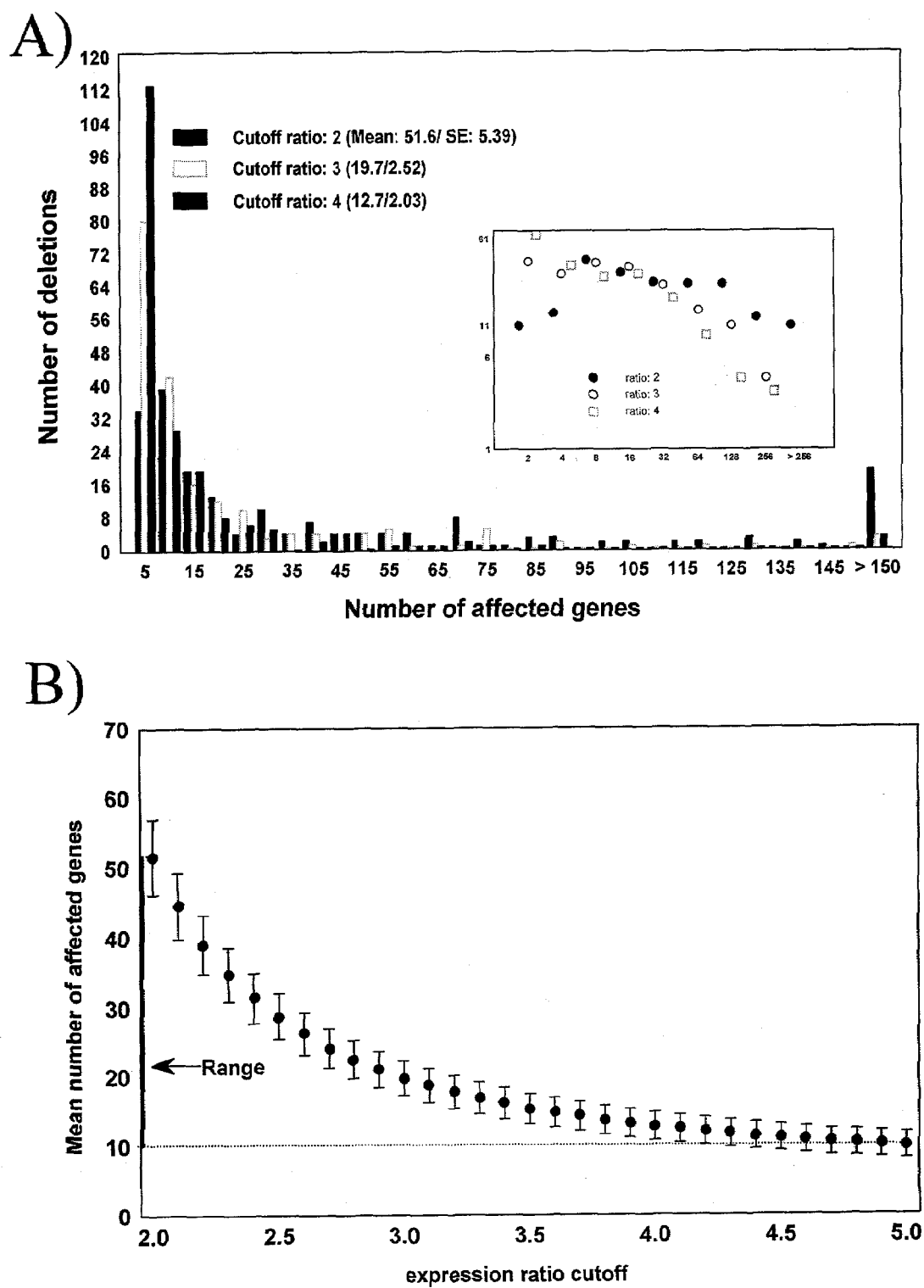
FIG. 14 illustrates the distribution of the number of genes whose mRNA expression levels changes as a result of a gene deletion for three different significance thresholds R of expression ratios and the mean and standard error of the number of genes whose expression ratio is affected by a genetic perturbation, as a function of the significance threshold R.

Data summarizing the effects of 271 gene deletions (and other treatments) on gene expression was made available as supplemental material to Hughes, T. R., M. J. Marton, A. R. Jones, C. J. Roberts, R. Stoughton et al., Functional discovery via a compendium of expression profiles. Cell 102: 109–126 (2000). From this data set, which contains $\log_2$-transformed expression ratios of 6312 strains for each mutation, the present inventor eliminated all data on haploid and aneuploid deletion strains, as well as data on non-genetic treatments. The present inventor analyzed the remaining data set of the effects of 196 gene deletions on the expression 6312 yeast genes. FIG. 14A shows the distribution of the number of genes whose mRNA expression levels changes as a result of a gene deletion for three different significance thresholds R of expression ratios. The inset shows the same distribution on a log-log scale. FIG. 14B shows the mean and standard error of the number of genes whose expression ratio is affected by a genetic perturbation, as a function of the significance threshold R. Averages are taken over the 196 genetic perturbations reported in Hughes et al. (2000). The mean number of affected genes varies between 9.9 (R=5; SE=1.84) and 51.6 (R=2; SE=1.89) genes.

Figure 15:
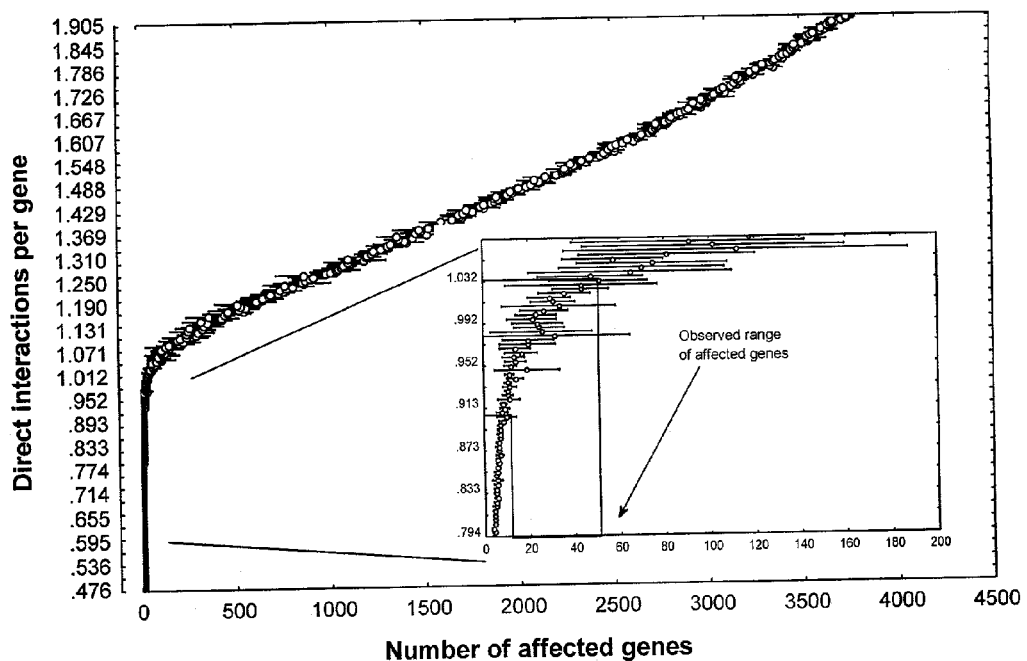
FIG. 15A–B illustrates the mean number of direct interactions per gene and the number of subnets in a random network as a function of the number of genes affected by a genetic perturbation.
Figure 15:
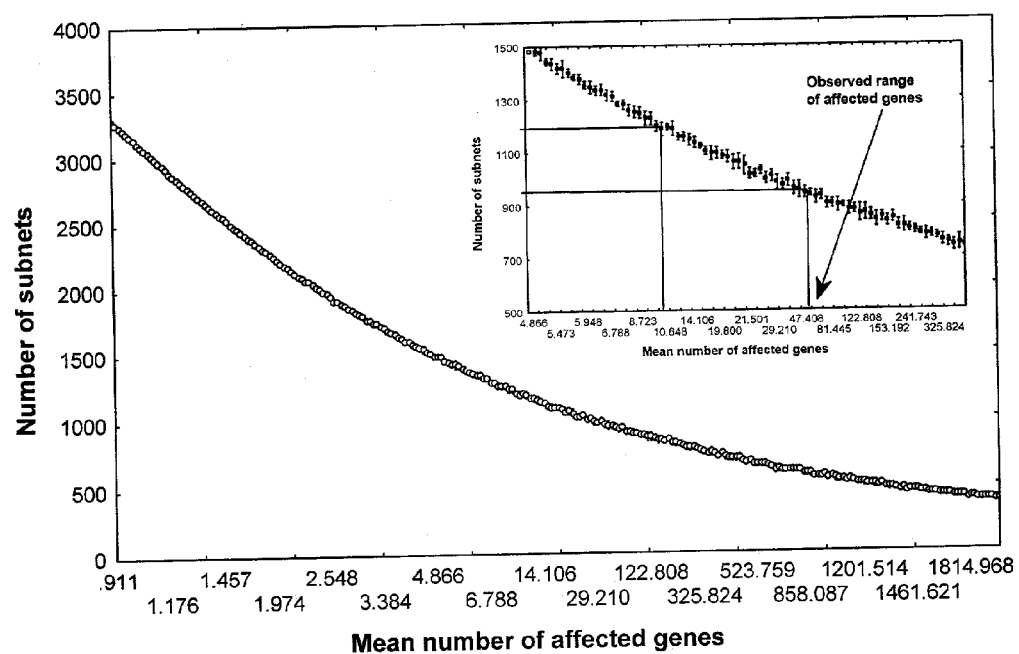

FIG. 15A shows the relation between the mean number of direct interactions per gene (y-axis) and the number of genes affected by a genetic perturbation (x-axis) for ten numerically generated Erdös-Rényi networks of n=6300 genes. The inset also shows the experimentally observed range (from FIG. 14B) of the mean number of genes whose mRNA expression is affected by a gene deletion. This range maps onto a narrow interval of direct regulatory interactions d per gene (0.9<d<1.05, approximately). Thus, the yeast transcriptional regulatory network appears very sparse, showing no more direct regulatory interactions than genes. (The maximally possible number of interactions would be $1.9 \times 10^7$, three orders of magnitudes higher.)

Figure 16:
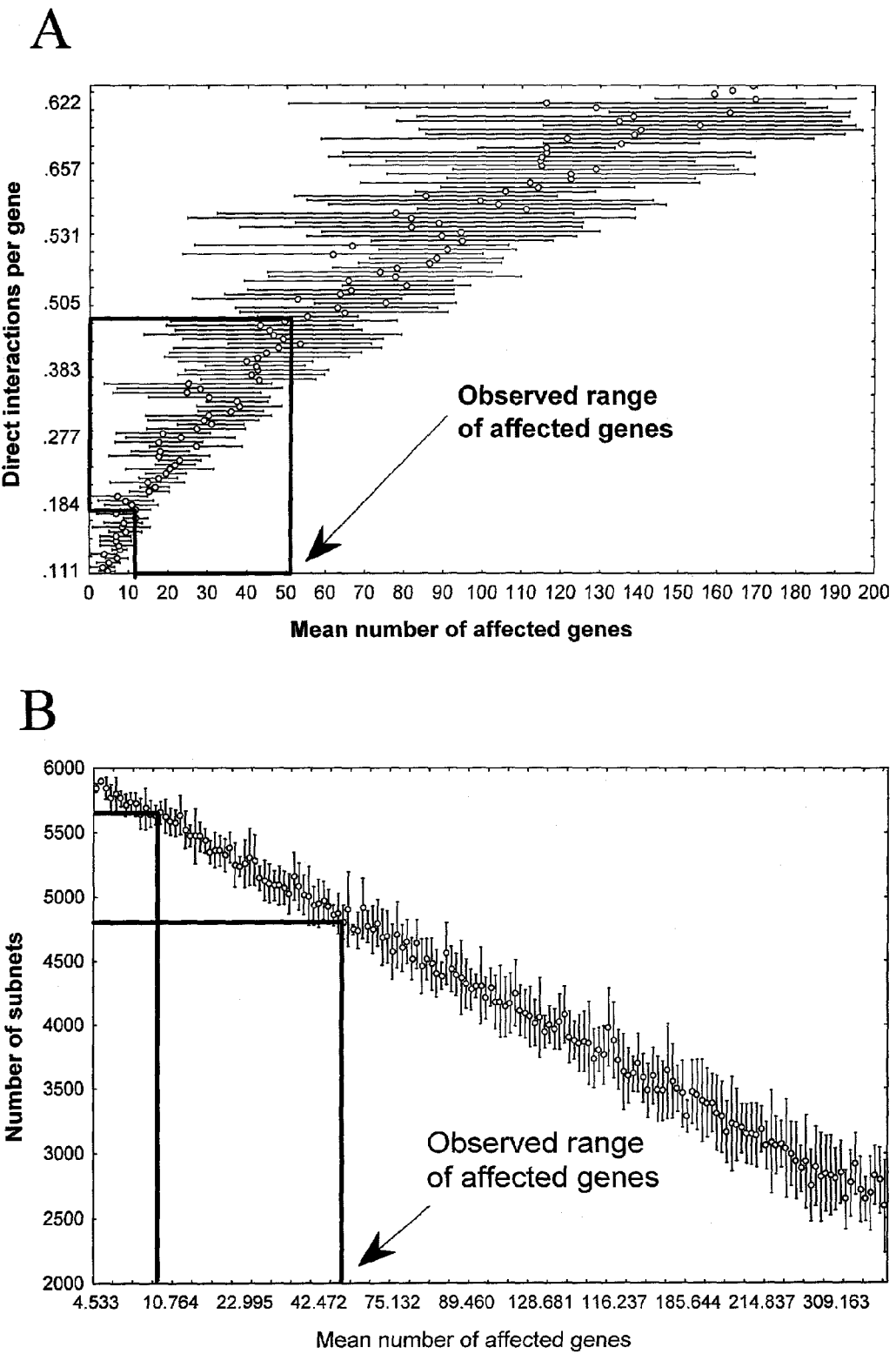
FIG. 16A–B illustrates the mean number of direct interactions per gene and the number of subnets in a random network as a function of the number of genes affected by a genetic perturbation

In comparison to ER networks with the same number of direct interactions, networks with a broad-tailed degree distribution generally show greater mean and variance in the number of genes affected by a perturbation. The reason lies in their disproportionately large number of genes with many direct interactions. This is exemplified by FIG. 16A, which shows numerical estimates from a network with n=6300 genes whose degree distribution follows a power law with $\tau=2$, an exponent within the range found for other biological networks. Networks with lower $\tau$ have even lower connectivity, but even networks with higher $\tau$ would have lower connectivity than ER networks. For $\tau=2$ the estimated number of direct interactions per gene falls within a range of 0.15<d<0.5 (FIG. 16A).

Gene perturbation data can also be used to derive a coarse picture of other network features. One such feature is the number of modules or subnets of a network, groups of genes that influence only each others expression, but not that of other genes. FIG. 15B shows the number of subnets as a function of the number of genes affected by a genetic perturbation for ER networks. For a network with 9.9<a<51.6 genes affected by a genetic perturbation, this relation implies between 1282 (σ=16.8; a=9.9) and 956 (σ=31; a=51.6) subnets, respectively. Many of these subnets are isolated genes, genes neither transcriptionally regulated nor regulating the mRNA expression of any other gene. More specifically, the expected number of isolated nodes in a sparse ER network with n nodes and k=nd edges is approximated by $n_0 \approx n[1-2k/(n(n-1))]^{n-1}$ For an ER network this leads to an estimated mean number of 185–241 subnets containing more than one gene (1282−1041=241 for a=9.9 and d=0.9; 956−771=185 for a=51.6 and d=1.05). FIG. 4B shows analogous results for networks whose interactions follow a power-law (τ=2). They contain between 5638 (σ=92; a=9.9) and 4584 (σ=153; a=51.6) subnets. Numerical estimates (not shown) of the number of isolated genes predict a mean number of 144–349 subnets containing more than one gene.

The crude estimates of subnets allows quantitative and qualitative assessments of the genetic networks, and the global connections. The pleiotropic effects of mutated genes will be revealed. The inventor anticipates that the number of nodules and the number of isolated genes are likely underestimates, because gene perturbation studies preferentially perturb a sample of "interesting" regulatory genes with many interactions, and not an unbiased random sample.

One might argue that the restriction to transcriptional regulation networks (imposed by experimental technology) compromises biological interpretation of network structure estimates. In this regard, it is worth keeping in mind that transcriptional regulation is ubiquitous, and that the endpoints of most regulatory pathways are transcriptionally regulated genes. Thus, while imperfect, a transcriptional regulation network provides a backbone around which more inclusive analyses can be organized.

The number of direct regulatory interactions in this network is of the order of the total number of genes. It may be much smaller if few genes are responsible for most interactions. The global yeast transcriptional regulatory network is thus very sparse. The cardinal weakness of the approach used to obtain this estimate is the need to assume, currently ad hoc, although supported anecdotally, a global network structure. However, the upper bound on network connectivity is robust to changes in network architecture. That genetic networks are very sparse is good news for methods to reconstruct them, without statistical assumptions, from perturbation experiments.

As, discussed above, FIG. 16A shows the mean numbers of direct interactions per gene (y-axis, the connectivity of the network) as a function of the mean number of genes affected by a genetic perturbation (x-axis). Each data point is a numerical estimate based on the mean (horizontal bars correspond to standard deviations) over 10 numerically generated networks with n=6300 genes. FIG. 16B shows the number of subnets in a random network as a function of the number of genes affected by a genetic perturbation. The boxed regions indicate the upper and lower boundaries of the mean number of genes affected by a perturbation, according to experimental data.

The estimates shown here are based on random graphs whose probability distribution P(d) of the number of direct interactions is proportional to $d^\tau$, for some constant τ. Such graphs, with a pre-specified number of n=6300 nodes and k edges were generated following a prescription by M. Newman (unpubl. manuscript). Briefly, a graph with n=6300 isolated nodes was generated. A node was then chosen at random from this graph. A random integer d>0 with the desired power law distribution was then assigned to this node in the following way. First, a random number d= $\lceil -\gamma^* \log(1-r) \rceil$ was generated, where r is a random real number uniformly distributed in the interval (0,1), and γ>0 is a constant (see below). The symbol $\lceil x \rceil$ refers to the smallest integer greater than x. Second, this number d was accepted with probability $d^{-\tau}$. If d was not accepted, it was discarded, and a new d was generated according to the same prescription, repeating this process until a d was accepted. Strictly speaking, the resulting distribution of d is a power law with an exponential cutoff, $P(d) \propto d^{-\tau} \exp(-d/\gamma)$. (Such a cutoff is necessary for graphs with τ<2. They are otherwise ill-defined, because their distribution P(d) diverges.) A large value of γ=1000 was used here, such that the distortion caused by the cutoff is negligible. Once a d was accepted, it was assigned to the randomly chosen node. Another node was chosen at random (without replacement of the previously chosen node), an integer d was assigned to it in the same way, and this process was repeated until the sum S of all the integers assigned to the chosen nodes first exceeded 2k. The integers assigned to each node correspond to the node's degree. They may also be thought of as the "stubs" of edges emerging from a node. Two such stubs were then chosen at random, and the respective nodes were connected via an edge, until the reservoir of stubs was exhausted, i.e., until S/2 edges had been placed on the graph.

Although the present invention has been described with respect to particular embodiments, many other embodiments are possible without departing from the scope of the present invention.

For example, although disclosed as a method and apparatus, the network graph produced thereby is also within the scope of the invention. Indeed, graphs characterizing entire networks as well as graphs for subsets and relationships between subsets are within the scope of the invention. There may also be situations where it is desirable to screen and characterize the relationship of a set or sets of genes. For example, it may be desirable to generate and compare adjacency lists for corresponding genes in different organisms.

As such, the present invention has additional utility including, but not limited to, characterizing and determining the structure of genetic networks, characterizing subsets of gene networks, identifying subsets of gene networks (in addition to individual genes since an entire subset may have desirable or undesirable effects), identifying a preferred target gene or gene set, identifying a preferential therapeutic candidate, identifying an altered gene path due to therapy (i.e., where the presence of a drug alters the path), determining network complexity to find the simplest or most direct networks, identifying a therapeutic candidate from the adjacency list, comparing two (or more) different networks for the same gene (i.e. identifying the same gene in a mouse versus a human and how the networks work), and identifying gene behavior in different organisms. Additionally, this method applies not only to experiments that determine qualitatively the effect of a perturbation on other genes (i.e., whether other genes change their activity or not), but also quantitatively (i.e., to what extent other genes change their activity).

Appendix A

Below is a perl implementation of the algorithm from FIG. 3. When given the accessibility list in FIG. 1C, i.e., the list of adjacent node pairs (p(u,v)=1), it produces as part of its output the adjacency list of FIG. 1B, except for node pairs (3,2), (6,12), and (13,8), which are shortcuts of the graph in FIG. 1A. The algorithm's structure follows exactly that of the pseudocode shown in FIG. 3 and explained in the main text, with one difference: only one data structure is used to represent both accessibility list and path lengths between nodes. This structure is a two-dimensional hashing array acc. The accessibility list needs to be read into this array (input and output are not shown here) such that after input but before the algorithm is run $acc{$u}{$v}=1 if gene $v is accessible from gene $u. This implies that $acc{$u}{$v } is also defined. If gene $v is not accessible from gene $u, then $acc{$u} {$v} must be undefined. The algorithm tests whether $v is accessible from $u by testing whether the corresponding entry of acc is defined, and it performs the path length maximization on the integer entries of acc. Initiating $acc{$u} {$v} to one for accessible nodes makes step 12 of FIG. 3 unnecessary. After execution, the defined entries of acc indicate the maximum path lengths between two nodes. Visited nodes are tracked by a one-dimensional hashing array % visited which needs to be initialized as '% visited=( );' before execution.

```
foreach $u (sort keys %acc) {
    if($visited{$u} !=1) {
        MAXPATH($u);
    }
}
sub MAXPATH    {
    # declare calling variable as local
    my $u=@_[0];
    #loop 1 of MAXPATH
    foreach $v (keys %{$acc{$u}})    {
        if($visited{$v} !=1)    {
            if (scalar(keys %{$acc{$v}}) == 0)    {
                $visited{$v} =1;
            }
            else {
                MAXPATH($v);
            }
        }
    }
    #loop 2 of MAXPATH
    foreach $v (keys %{$acc{$u}} ) {
        foreach $w (keys %{$acc{$v}})    {
            $tmp=$acc{$u}{$v} + $acc{$v}{$w};
            if ($tmp > $acc{$u}{$w} ) {
                $acc{$u}{$w}=$tmp;
            }
        }
    }
    $acc{$u}{$v}=0;
    $visited{$u}=1;
}# end subroutine MAXPATH
```

Appendix B

Below is a perl implementation of the algorithm to reconstruct acyclic genetic networks by pruning accessibility lists. Its structure follows exactly that of the pseudocode shown in FIG. 9 and explained in the main text, with one difference. Only one data structure is used to represent both accessibility list and adjacency list. This structure is a two-dimensional hashing array acc. The accessibility list needs to be read into this array (input and output are not shown here) such that after input but before the algorithm is run $acc {$i } {$j }=1 if gene $j accessible from gene $i. This implies that $acc{$i} {$j} is also defined. If gene $j is not accessible from gene $i, then $acc{$i} {$j} must be undefined. The algorithm tests whether $j is accessible from $i by testing whether the corresponding entry of acc is defined, but it prunes acc by setting an entry to zero. After execution, all entries of acc that are still equal to one are entries of adj and can be read out that way. Visited nodes are kept track of by a one-dimensional hashing array % visited which needs to be initialized as '%visited=( );' before execution. I do not claim that this is the most efficient or most elegant implementation.

```
# master loop
foreach $i(sort keys %acc)    {
    if($visited{$i} !=1)    {
        PRUNE_ACC($i);
    }
}
sub PRUNE_ACC    {
    # declare calling variable as local
    my $i=@_[0];
    # loop one of PRUNE_ACC
    foreach $j (keys %{$acc{$i}})    {
        if($visited{$j} !=1)    {
            if (scalar(keys %{$acc{$j}}) ==0)    {
                $visited{$j}=1;
            }
            else {
                PRUNE_ACC($j);
            }
        }
    }
    #loop two of PRUNE_ACC
    foreach $j (keys %{$acc{$i}})    {
        foreach $k (keys %{$acc{$j}} )    {
            if($acc{$j}{$k}==1)    {
                if ($acc{$i}{$k}==1)    {
                    $acc{$i}{$k}=0;
                }
            }
        }
    }
    $visited{$i}=1;
}
```

I claim:

1. A method for determining all direct and indirect genetic interactions in a graph representation of a genetic network of an organism, comprising:
    obtaining a first accessibility list of said graph representation of said genetic network from appropriate genetic perturbation data;
    applying graph theory mathematics to the first accessibility list and its graph to determine a condensation of the graph as defined by the condensation's accessibility list;
    applying graph theory mathematics to the condensation's accessibility list to determine an adjacency list characterizing all direct and indirect genetic interactions in said genetic network.

2. The method of claim 1, wherein said graph theory mathematics are applied using a recursive algorithm.

3. The method of claim 2, wherein said recursive algorithm determines the adjacency list of a most parsimonious graph.

4. The method of claim 2, wherein said recursive algorithm determines a list of the longest path of said graph.

5. The method of claim 2, wherein said recursive algorithm implements steps comprised in pseudocode below:

```
1    for all nodes i of G
2        if component [i] has not been defined
3            create new node x of G*
4            component [i]=x
```

```
5       for all nodes j ∈ Acc(i)
6           if i∈Acc(j)
7               component [j]=x
8           end if
9       end if
10  for all nodes i of G*
11      Acc G* (i)=∅
12  for all nodes I of G
13      for all nodes j∈ Acc(i)
14          if component[i]≠ component [j]
15              if component[j] ∈Acc G* (component [i])
16                  add component [j] to Acc G* (component [i])
17              end if
18          end if
``` wherein Acc(i) is an accessibility list of node i, Adj(i) is an adjacency list of node i, nodes j are those accessible from the calling node i, G is the graph of the genetic network, and G* is the condensation graph, and component [j] is a data structure which is an array indexed by nodes j.

6. The method of claim 4, wherein said recursive algorithm implements steps comprised in pseudocode below:

```
1   for all nodes u of G
2       if node u has not been visited
3           call MAXPATH(u)
4       end if
5   MAXPATH(u)
6       for all nodes v∈Acc(u)
7           if Acc(v)=∅
8               declare v as visited.
9           else
10              call MAXPATH(v)
11          end if
12          p(u,v)=1
13          for all nodes v∈ Acc(u)
14              for all nodes w∈ Acc(v)
15                  p(u,w)=max(p(u,w), 1+p(v,w))
16      p(u,u)=0
17      declare node u as visited
18  end MAXPATH(u)
``` wherein p is pathlength, G is the genetic network graph, Acc is the accessibility list of G.

7. The method of claim 2, wherein said recursive algorithm implements steps comprised in pseudocode below:

```
1   for all nodes i of G
2       Adj(i)=Acc(i)
3   for all nodes i of G
4       if node i has not been visited
5           call PRUNE_ACC(i)
6       end if
7   PRUNE_ACC(i)
8       for all nodes j∈Acc(i)
9           if Acc(i)=∅
10              declare j as visited
11          else
12              call PRUNE_ACC(j)
13          end if
14      for all nodes j∈Acc(i)
15          for all nodes k∈Acc(j)
16              if k∈Acc(i)
17                  delete k from Adj(i)
18          end if
19      declare node i as visited
20  end PRUNE_ACC(i)
``` where G is the graph, G* is the condensation of the graph G, component [i] is a data structure which is an array indexed by nodes i of G and pointing to a node of G* which corresponds to a component in which i resides, each j is a node accessible from each node i, and component [j] is a data structure which is an array indexed by nodes j.

8. The method of claim 1, wherein said genetic perturbation data and resulting adjacency list are selected from a group consisting of: all genes of an organism whose activity has been measured, all genes of a genetic network of an organism whose activity has been measured, and all genes of a genetic sub-network of an organism whose activity has been measured.

9. The method of claim 1 wherein said gene perturbation data is associated with an animal and is related to genetic interactions.

10. The method of claim 9 wherein the genetic interactions comprise tolerance to biotic or abiotic environmental stress.

11. A system for determining all direct and indirect genetic interactions in a graph representation of a genetic network of an organism, comprising:
 a general purpose computer;
 software instructions operating on said computer and adapted to input a first accessibility list from appropriate genetic perturbation data;
 additional software instructions operating on said computer and adapted to apply graph theory mathematics to the first accessibility list and its graph to determine a condensation of the graph as defined by the condensation's accessibility list;
 further software instructions operating on said computer and adapted to applying graph theory mathematics to the condensation's accessibility list to determine an adjacency list characterizing all direct and indirect genetic interactions in said genetic network.

12. The system of claim 11, further comprising software instructions operating on said computer and adapted to produce a graph representation of a structure of said genetic network.

* * * * *